US009949945B2

(12) United States Patent
Withers et al.

(10) Patent No.: US 9,949,945 B2
(45) **Date of Patent: *Apr. 24, 2018**

(54) 3' EQUATORIAL-FLUORINE-SUBSTITUTED NEURAMINIDASE INHIBITOR COMPOUNDS, COMPOSITIONS AND METHODS FOR THE USE THEREOF AS ANTI-VIRALS

(71) Applicant: THE UNIVERSITY OF BRITISH COLUMBIA, Vancouver (CA)

(72) Inventors: Stephen Withers, Vancouver (CA); Hongming Chen, Vancouver (CA); Ricardo Resende, Vancouver (CA); Jennifer Lois Breschkin, Essendon (AU)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/243,679

(22) Filed: Aug. 22, 2016

(65) Prior Publication Data

US 2017/0165223 A1 Jun. 15, 2017

Related U.S. Application Data

(63) Continuation of application No. 14/372,820, filed as application No. PCT/CA2013/050034 on Jan. 17, 2013, now Pat. No. 9,637,465.

(Continued)

(51) Int. Cl.
*A61K 31/35* (2006.01)
*A61K 31/351* (2006.01)

(52) U.S. Cl.
CPC .................................. *A61K 31/351* (2013.01)

(58) Field of Classification Search
CPC ............................ C07D 309/14; A61K 31/351
(Continued)

(56) References Cited

U.S. PATENT DOCUMENTS

| | | | |
|---|---|---|---|
| 5,360,817 | A | 11/1994 | Izstein et al. |
| 6,204,029 | B1 | 3/2001 | Withers et al. |

(Continued)

FOREIGN PATENT DOCUMENTS

| | | |
|---|---|---|
| WO | 1995023157 | 8/1995 |
| WO | 2004043488 | 5/2004 |

(Continued)

OTHER PUBLICATIONS

Buchini et al. (2008) "Towards a New Generation of Specific Trypanosoma cruzi Trans-Sialidase Inhibitors" Angew Chemie Int Ed Engl 47(14):2700-2703.

(Continued)

*Primary Examiner* — Taylor V Oh
(74) *Attorney, Agent, or Firm* — Rudy J. Ng; Carol L. Francis; Bozicevic, Field & Francis LLP

(57) ABSTRACT

Equatorial 2,3-fluorinated glycosides compounds of formula (I) useful for the treatment or prophylaxis of viral infection, particularly viral influenza, the methods for their preparation, and their pharmaceutical compositions are provided. The therapeutic effect is achieved via inhibition of viral neuraminidases.

17 Claims, 4 Drawing Sheets

Related U.S. Application Data

(60) Provisional application No. 61/588,577, filed on Jan. 19, 2012.

(58) Field of Classification Search
USPC .......................................... 514/459; 549/356
See application file for complete search history.

(56) References Cited

U.S. PATENT DOCUMENTS

| | | | | |
|---|---|---|---|---|
| 6,284,494 | B1 | 9/2001 | Withers et al. | |
| 8,815,941 | B2 | 8/2014 | Withers et al. | |
| 8,907,111 | B2 | 12/2014 | Withers et al. | |
| 9,221,859 | B2 | 12/2015 | Withers et al. | |
| 9,382,284 | B2 | 7/2016 | Withers et al. | |
| 9,637,465 | B2 * | 5/2017 | Withers | C07D 309/14 |
| 2014/0350095 | A1 | 11/2014 | Withers et al. | |
| 2016/0068501 | A1 | 3/2016 | Withers et al. | |
| 2017/0022177 | A1 | 1/2017 | Withers et al. | |

FOREIGN PATENT DOCUMENTS

| | | | |
|---|---|---|---|
| WO | 2010029302 | | 3/2010 |
| WO | 2011006237 | | 1/2011 |
| WO | WO2011006237 | * | 1/2011 |

OTHER PUBLICATIONS

Carvalho Leonardo J M et al. (2005) "Immunization of Saimiri sciureus monkeys with a recombinant hybrid protein derived from the Plasmodium falciparum antigen glutamate-rich protein and merozoite surface protein 3 can induce partial protection with Freund and montanide ISA720 Adjuvants," Clinical and Diagnostic Laboratory Immunology, 12: 2: 242-248.
Hagiwara, et al. (1994) "Inhibition of Bacterial and Viral Sialidases by 3-Fluoro-N-Acetylneuraminic Acid" Carbohydr Res 263(1):167-172.
Theisen M et al. (2004) IIA Plasmodium falciparum 11-21GLURP-MSP3 chimeric protein; expression in Lactococcus lactis, immunogenicity and induction of biologically active antibodies 11, Vaccine, 22: 9-10:1188-1198.
U.S. Appl. No. 13/382,284, filed Mar. 26, 2012, Issued as 8,815,941.
U.S. Appl. No. 13/354,254, filed Jan. 19, 2012, Issued as 8,907,111.
U.S. Appl. No. 14/533,903, filed Nov. 5, 2014, Issued as 9,382,284.
U.S. Appl. No. 15/162,055, filed May 23, 2016, published as US 2017/0022177.
U.S. Appl. No. 14/330,855, filed Jul. 14, 2014, Issued as 9,221,859.
U.S. Appl. No. 14/946,132, filed Nov. 19, 2015, published as US 2016/0068501.
U.S. Appl. No. 14/372,820, filed Jul. 17, 2014, published as US 2014/0350095.
Amaya et al. (2004) "Structural insights into the catalytic mechanism of Trypanosoma cruzi trans-sialidase" Structure 12(5):775-784.
Bantia et al. (2001) "Comparison of the anti-influenza virus activity of RWJ-270201 with those of oseltamivir and zanamivir" Antimicrob Agents Chemother 45(4):1162-7.
Barrett, S. et al. (2011) PLoS One 6, e23627.
Berge et al. (1977) "Pharmaceutical Salts" J. Pharm. Sci. 66(1):1-19.
Cantarel et al. (2009) "The Carbohydrate-Active EnZymes database (CAZy): an expert resource for Glycogenomics" Nucleic Acids Res 37:D233-238.
Chandler et al. (1995) "Synthesis of the Potent Influenza Neuraminidase Inhibitor 4-Guanidino Neu5Ac2en. X-Ray Molecular Structure of 5-Acetamido-4-Amino-2,6-Anhydro-3,4,5-Trideoxy-D-Erythro-L-Gluco-Nononic Acid" J Chem Soc. Perk. Trans 1 9:1173-1180.
Damager et al. (2008) "Kinetic and Mechanistic Analysis of Trypanosoma cruzi Trans-sialidase Reveals a Classical Ping-Pong Mechanism with Acid/Base Catalysis" Biochemistry, 47(11):3507-3512.
Henrissat and Davies (1997) "Structural and sequence-based classification of glycoside hydrolases" Structural Biology 7:637-644.
Ikeda et al. (2004) "2β,3β-Difluorosialic acid derivatives structurally modified at the C-4 position: synthesis and biological evaluation as inhibitors of human parainfluenza virus type 1" Carbohydrate Res. 339(7):1367-72.
Ikeda et al. (2006) "2-Deoxy-2,3-didehydro-N-acetylneuraminic acid analogues structurally modified at the C-4 position: synthesis and biological evaluation as inhibitors of human parainfluenza virus type 1" Bioorg Med Chem 14 (23):7893-7897.
Kim et al (2009) "Development of New and Selective Trypanosoma cruzi trans-Sialidase Inhibitors from Sulfonamide Chalcones and their Derivatives" ChemBioChem 10:2475-2479.
Leneva et al. (2001) "Efficacy of zanamivir against avian influenza A viruses that possess genes encoding H5NI internal proteins and are pathogenic in mammals" Antimicrob Agents Chemother 45(4):1216-24.
Morley et al. (2009) "Bacteriophage KIF Endo-Sialidase is an Inverting Glycosidase" The Journal of Biological Chemistry 284:17404-17410.
Newstead et al. (2008) "The structure of Clostridium perfringens Nanl sialidase and its catalytic intermediates" J. Biol Chem 283:9080-9088.
Tisdale (2000) "Monitoring of viral susceptibility: new challenges with the development of influenza NA inhibitors" Rev Med Viral 10(1):45-55.
Von Itzstein, M. et al. (1993) "A convenient method for the introduction of nitrogen and sulfur at C-4 on a sialic acid analogue" Carbohydr. Res. 244(1): 181-185.
Von Itzstein (2007) "The war against influenza: discovery and development of sialidase inhibitors" Nat Rev Drug Discov 6(12):967-974.
Watts et al (2003) "Trypanosoma cruzi Trans-sialidase Operates through a Covalent Sialyi-Enzyme Intermediate: Tyrosine is the Catalytic Nucleophile" J. Am. Chem. Soc. 125:7532-7533.
Watts and Withers (2004) "The synthesis of some mechanistic probes for sialic acid processing enzymes and the labeling of a sialidase from Trypanosoma rangeli" Can_ J. Chem. 82:1581-1588.
Watts et al. (2006) "Structural and Kinetic Analysis of Two Covalent Sialosyl-Enzyme Intermediates on Trypanosoma rangeli Sialidase" J Biol Chem 281:4149-4155.
Withers & Aebersold (1995) "Approaches to labeling and identification of active site residues in glycosidases" Protein Sci 4(3):361-372.
Zbiral et al. (1989) "Synthesis of the 4-acetamido-4-deoxy analogue of N-acetylneuraminic acid and its behaviour towards CMP-sialate synthase" Carbohydr Res 194:C I5-C18.

* cited by examiner

3' EQUATORIAL-FLUORINE-SUBSTITUTED NEURAMINIDASE INHIBITOR COMPOUNDS, COMPOSITIONS AND METHODS FOR THE USE THEREOF AS ANTI-VIRALS

TECHNICAL FIELD

This invention relates to therapeutics, their uses and methods for the treatment or prophylaxis of viral infection. In particular the invention relates to compounds, compositions, therapies, and methods of treatment for viral infections such as influenza.

BACKGROUND

Infection and invasion by influenza viruses requires the intermediacy of sialic acid residues on the surface of the host cell. The terms sialic acid and neuraminic acid are used interchangeably. Similarly, sialidase and neuraminidase (NA) are used interchangeably. Initial attachment of the virus to the host cell occurs via the binding of the virus to these sialic acids (charged, 9-carbon sugars) through the hemagglutinin protein of the virus. Once inside the cell the virus replicates by taking advantage of the host cellular machinery. However, in order to remain optimally infective, the virus has evolved an NA that cuts off the sialic acid from the host cell surface to assist the virus in escaping the host cell to infect other cells. Failure to cut off the sialic acid from the host cell surface, results in retention of virus through attachment to the host cell.

The GH33 family of neuraminidases contains all the sialidases except the viral enzymes (GH34 family). The GH33 and GH34 families are distinct structurally and by sequence (See Cantarel B L. et al. (2009); and Henrissat B. and Davies G J (1997) for background on Family classifications). Previous work has demonstrated that 2,3-difluorosialic acids (DFSAs) are effective inhibitors of GH33 NAs and that GH33 NAs proceed through a covalent intermediate (see for example, Watts, A. et al. (2003); Amaya, M. F. et al. (2004); Watts, A. G. and Withers, S. G. (2004); Watts, A. G. et al. (2006); Newstead, S. et al. (2008); Damager, I. et al. (2008); and Buchini, S. et al. (2008)). The most probable mechanism for the GH34 sialidase (i.e. viral sialidases) reported in the literature is one involving an ion-pair intermediate (von Itzstein M. (2007)).

A number of compounds are known to inhibit NAs. Some well known NA inhibitors are alkene-containing sialic acid analogues (for example: Laninamivir CAS #203120-17-6; Oseltamivir (Tamiflu) CAS #204255-11-8; and Zanamivir (Relenza) CAS # 139110-80-8; see also U.S. Pat. No. 5,360,817; and Ikeda et al. Bioorganic & Medicinal Chemistry (2006) 14:7893-7897). Fluorinated sugar derivatives with (reactive) fluoride leaving groups have been shown to be inhibitors of a range of “retaining” glycosidases and function via formation of particularly stable glycosyl-enzyme intermediates (for example, Zechel and Withers ((2000) Accounts of Chemical Research 33, 11-18) and Buchini et al. (2008)). These reagents are quite specific with respect to their target enzymes, have been shown to be highly bio-available, and even capable of crossing the blood-brain barrier. Such inhibitors are mechanism-based in their action, making the development of resistance by viruses difficult, whereby any mutations in the viral enzyme that reduce the inhibition must necessarily reduce the efficiency of the enzyme on the natural substrate, sialic acid and therefore less likely to be tolerated. The initial design of oseltamivir and zanamivir was based upon the mimicry of the flattened transition state conformation of the sugar through incorporation of an endocyclic alkene within a carbocycle (oseltamivir) or a pyranose ring (zanamivir) (M. von Itzstein et al., *Nature* 363, 418 (1993)). Specificity for the influenza enzyme over other NAs, along with additional affinity, was provided by incorporation of a guanidinium or ammonium substituent at the position corresponding to C-4 of the natural substrate to interact with a highly conserved anionic pocket at that location in the active site. These broad spectrum influenza drugs are active against NAs from group 1 and 2 influenza A strains as well as influenza B.

Despite being transition state analogue inhibitors, the emergence of drug-resistant strains has been reported, particularly against the more widely used and structurally divergent drug oseltamivir. Mutations can be both drug- and influenza subtype-specific. The most commonly seen mutation in viruses with the N1 subtype is H275Y which interferes with binding of the isopentyl side chain of oseltamivir, but still permits binding of zanamivir and the natural substrate. Mutations most commonly detected in clinical isolates with the N2 subtype include R292K (J. L. McKimm-Breschkin et al., *J. Virol.* 72, 2456 (1998); M. Tashiro et al., *Antivir. Ther.* 14, 751 (2009); M. Kiso et al., *Lancet* 364, 759 (2004)) and E119V (M. Tashiro et al., *Antivir. Ther.* 14, 751 (2009); M. Kiso et al., *Lancet* 364, 759 (2004)). Like the H275Y, the R292K precludes full rotation of the E276 necessary to create the hydrophobic pocket that accommodates the pentyl side-chain of oseltamivir (J. N. Varghese et al., *Structure* 6, 735 (1998)). In contrast, E119V confers oseltamivir specific resistance due to altered interactions with the 4-amino group. E119A, D, G mutations seen in vitro (T. J. Blick et al., *Virology* 214, 475 (1995); L. V. Gubareva et al., *J. Virol.* 71, 3385 (1997)) affect binding of oseltamivir and/or zanamivir, demonstrating the significance of the interactions of C-4 amino or guanidino group for high affinity binding. Some of the recent mutations seen in pandemic H1N1 viruses, including I223R, confer reduced sensitivity to both inhibitors (A. Eshaghi et al., *Emerg. Infect. Dis.* 17, 1472 (2011); H. T. Nguyen et al., *Clin. Infect. Dis.* 51, 983 (2010); E. van der Vries et al., *N. Engl. J. Med.* 363, 1381 (2010)). The emergence of mutant strains suggests that new neuraminidase inhibitors with increased propensity to maintain potency against such mutant viral strains would be of interest.

SUMMARY

This invention is based in part on the fortuitous discovery that compounds having a 3' equatorial fluorine (F), as described herein, have surprisingly good neuraminidase modulatory properties. Specifically, compounds identified herein, show prolonged inhibition of neuraminidase, which may be useful for the treatment or prophylaxis of viral infection. In particular, compounds identified herein may be useful for the treatment or prophylaxis of influenza. Moreover, the subject compositions exhibit a greater propensity to maintain potency against particular mutant viral strains as compared to corresponding stereoisomer compositions having a 3' axial F configuration and other related compositions.

The compounds described herein may be used for in vivo or in vitro research uses (i.e. non-clinical) to investigate the mechanisms of neuraminidase inhibition. Furthermore, these compounds may be used individually or as part of a kit for in vivo or in vitro research to investigate neuraminidase inhibition using recombinant proteins, viral strains, cells maintained in culture, and/or animal models. Alternatively, the compounds described herein may be combined with commercial packaging and/or instructions for use.

This invention is also based in part on the discovery that the compounds described herein, may also be used to modulate neuraminidase activity either in vivo or in vitro for both research and therapeutic uses. The compounds may be used in an effective amount so that neuraminidase activity may be modulated. The neuraminidase may be viral. The neuraminidase may be an influenza neuraminidase. In particular, the compounds may be used to inhibit viral neuraminidase activity. The compounds modulatory activity may be used in either an in vivo or an in vitro model for the study of viral infection. For example, influenza infection. Furthermore, the compounds modulatory activity may be used for the treatment or prophylaxis of viral infection. The viral infection may be influenza.

In accordance with one embodiment, there are provided compounds having a 3' equatorial configuration of Formula I:

I

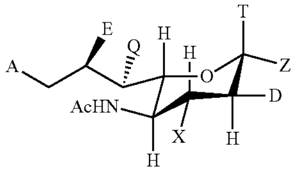

wherein T may be COOH or $COOR^1$, wherein $R^1$ may be a $C_{1-20}$ linear, branched or cyclic, saturated or unsaturated, unsubstituted alkyl group, Z may be F, or Cl; D may be F, or Cl; X may be $NH_2$, $NHC(NH)NH_2$, $NHCH_3$, $NHCH_2CH_3$, $NHCH_2CH_2CH_3$, $NHCH_2CH_2CH_2CH_3$, or $NHC(CH_3)CH_3$; Q may be OH, OMe, or OAc; E may be OH, or OAc; and A may be OH, or OAc.

In accordance with a further embodiment, there is provided a 3' equatorial compound, having the formula:

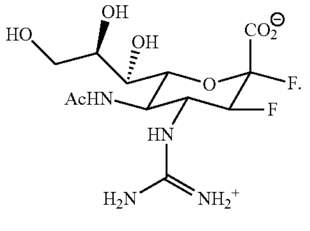

In accordance with a further embodiment, there is provided a 3' equatorial compound having the formula:

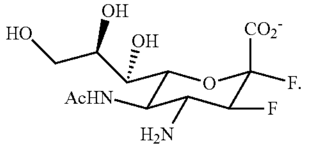

In accordance with a further embodiment, there are provided compounds as described herein for modulating viral neuraminidase activity. The viral neuraminidase may be a GH34 neuraminidase. The modulating of viral neuraminidase activity may be for the treatment of influenza in an animal. The animal may be a mammal. The animal may be a human.

In accordance with a further embodiment, there are provided compounds as described herein for use in the preparation of a medicament for modulating viral neuraminidase activity. The viral neuraminidase may be a GH34 neuraminidase. The modulating of viral neuraminidase activity may be for the treatment of influenza in an animal. The animal may be a mammal. The animal may be a human.

In accordance with a further embodiment, there are provided compounds as described herein for use in modulating viral neuraminidase activity. The viral neuraminidase may be a GH34 neuraminidase. The modulating of viral neuraminidase activity may be for the treatment of influenza in an animal. The animal may be a mammal. The animal may be a human.

In accordance with a further embodiment, there are provided pharmaceutical compositions which may include one or more compounds as described herein, or pharmaceutically acceptable salts thereof, and a pharmaceutically acceptable excipient. The pharmaceutical compositions are useful for modulating viral neuraminidase activity. The viral neuraminidase may be a GH34 neuraminidase. The modulating of viral neuraminidase activity may be for the treatment of influenza in an animal. The animal may be a mammal. The animal may be a human.

In accordance with a further embodiment, there are provided pharmaceutically acceptable salts of compounds described herein for modulating viral neuraminidase activity. The viral neuraminidase may be a GH34 neuraminidase. The modulating of viral neuraminidase activity may be for the treatment of influenza in an animal. The animal may be a mammal. The animal may be a human.

In accordance with a further embodiment, there is provided a method of modulating viral neuraminidase activity with one or more compounds described herein or a pharmaceutically acceptable salt(s) thereof, or a pharmaceutical composition comprising the same. In a further embodiment, there is provided a method of inhibiting viral neuraminidase activity. The viral neuraminidase may be a GH34 neuraminidase. The modulating of viral neuraminidase activity may be for the treatment of influenza in an animal. The animal may be a mammal. The animal may be a human.

In accordance with a further embodiment, there is provided a commercial package which may contain one or more compounds described herein or a pharmaceutically acceptable salt thereof or a pharmaceutical composition thereof. The commercial package may optionally contain instructions for the use of the compounds or pharmaceutically acceptable salt(s) thereof or pharmaceutical composition comprising the same in the treatment of influenza.

In accordance with a further embodiment, there is provided a method of modulating viral neuraminidase activity comprising the use of a 3' equatorial compound described herein or a pharmaceutically acceptable salt thereof, or a pharmaceutical composition comprising the same, wherein the compound (or pharmaceutically acceptable salt thereof) has at least about 2 fold better maintenance of potency as against a mutant virus as compared to its corresponding stereoisomer having a 3' axial configuration. In one embodiment, the method involves the use of more than one 3' equatorial compound provided herein, wherein at least one of the compounds has at least about 2 fold better maintenance of potency as against a mutant virus as compared to its corresponding stereoisomer having a 3' axial configuration.

Furthermore, 3' equatorial compounds may be used in combination with non-formula 1 compounds (for example, 3' axial compounds) for combination therapy.

In accordance with a further embodiment, there is provided a method of modulating viral neuraminidase activity with one or more compounds described herein or a pharmaceutically acceptable salt thereof, wherein the composition having 3' equatorial configuration, has at least about 2 fold better maintenance of potency as against a resistant virus as compared to the corresponding stereoisomer having a 3' axial configuration.

In accordance with a further embodiment, there is provided a method of modulating viral neuraminidase activity with one or more compounds described herein or a pharmaceutically acceptable salt thereof, wherein the composition having 3' equatorial configuration, has at least about 2 fold better maintenance of potency as against a virus as compared to the corresponding stereoisomer having a 3' axial configuration.

In accordance with a further embodiment, there is provided a method of modulating viral neuraminidase activity with one or more compounds described herein or a pharmaceutically acceptable salt thereof, wherein the composition having 3' equatorial configuration, has at least about 2 fold increase in specificity for a viral neuraminidase target (i.e. ki/Ki value) as compared to the corresponding stereoisomer having a 3' axial configuration.

In accordance with a further embodiment, there is provided a method of modulating viral neuraminidase activity with one or more compounds described herein or a pharmaceutically acceptable salt thereof, wherein the composition having 3' equatorial configuration, has at least about 3 fold increase in specificity (i.e. ki/Ki value) as compared to the corresponding stereoisomer having a 3' axial configuration.

In accordance with a further embodiment, there is provided a method of modulating viral neuraminidase activity with one or more compounds described herein or a pharmaceutically acceptable salt thereof, wherein the composition having 3' equatorial configuration, has at least about 4 fold increase in specificity (i.e. ki/Ki value) as compared to the corresponding stereoisomer having a 3' axial configuration.

In accordance with a further embodiment, there is provided a method of modulating viral neuraminidase activity with one or more compounds described herein or a pharmaceutically acceptable salt thereof, wherein the composition having 3' equatorial configuration, has at least about 5 fold increase in specificity (i.e. ki/Ki value) as compared to the corresponding stereoisomer having a 3' axial configuration.

In accordance with a further embodiment, there is provided a method of modulating viral neuraminidase activity with one or more compounds described herein or a pharmaceutically acceptable salt thereof, wherein the composition having 3' equatorial configuration, has at least about 10 fold increase in specificity (i.e. ki/Ki value) as compared to the corresponding stereoisomer having a 3' axial configuration.

In accordance with a further embodiment, there is provided a method of modulating viral neuraminidase activity with one or more compounds described herein or a pharmaceutically acceptable salt thereof, wherein the composition having 3' equatorial configuration, has at least about 15 fold increase in specificity (i.e. ki/Ki value) as compared to the corresponding stereoisomer having a 3' axial configuration.

In accordance with a further embodiment, there is provided a method of modulating viral neuraminidase activity with one or more compounds described herein or a pharmaceutically acceptable salt thereof, wherein the composition having 3' equatorial configuration, has at least about 19 fold increase in specificity (i.e. ki/Ki value) as compared to the corresponding stereoisomer having a 3' axial configuration.

In accordance with a further embodiment, there is provided a method of modulating viral neuraminidase activity with one or more compounds described herein or a pharmaceutically acceptable salt thereof, wherein the composition having 3' equatorial configuration, has at least about 20 fold increase in specificity (i.e. ki/Ki value) as compared to the corresponding stereoisomer having a 3' axial configuration.

In accordance with a further embodiment, there is provided a method of modulating viral neuraminidase activity with one or more compounds described herein or a pharmaceutically acceptable salt thereof, wherein the composition having 3' equatorial configuration, has at least about 25 fold increase in specificity (i.e. ki/Ki value) as compared to the corresponding stereoisomer having a 3' axial configuration.

In accordance with a further embodiment, there is provided a method of modulating viral neuraminidase activity with one or more compounds described herein or a pharmaceutically acceptable salt thereof, wherein the composition having 3' equatorial configuration, has at least about 30 fold increase in specificity (i.e. ki/Ki value) as compared to the corresponding stereoisomer having a 3' axial configuration.

In accordance with a further embodiment, there is provided a commercial package comprising one or more compounds or composition having 3' equatorial configuration described herein or a pharmaceutically acceptable salt thereof as described herein and instructions for the use in modulating viral neuraminidase activity.

T may be COOEt; Z may be F; D may be F; X may be $NH_2$ or $NHC(NH)NH_2$; Q may be OH; E may be OH; and A may be OH.

T may be COOH; Z may be F; D may be F; X may be $NH_2$ or $NHC(NH)NH_2$; Q may be OH; E may be OH; and A may be OH.

T may be COOH; Z may be F; D may be F; X may be $NH_2$; Q may be OH; E may be OH; and A may be OH.

T may be COOH; Z may be F; D may be F; X may be $NHC(NH)NH_2$; Q may be OH; E may be OH; and A may be OH.

$R^1$ may be $C_{1-19}$. $R^1$ may be $C_{1-18}$. $R^1$ may be $C_{1-17}$. $R^1$ may be $C_{1-16}$. $R^1$ may be $C_{1-15}$. $R^1$ may be $C_{1-14}$. $R^1$ may be $C_{1-13}$. $R^1$ may be $C_{1-12}$. $R^1$ may be $C_{1-11}$. $R^1$ may be $C_{1-10}$. $R^1$ may be $C_{1-9}$. $R^1$ may be $C_{1-8}$. $R^1$ may be $C_{1-7}$. $R^1$ may be $C_{1-6}$. $R^1$ may be $C_{1-5}$. $R^1$ may be $C_{1-4}$. $R^1$ may be $C_{1-3}$. $R^1$ may be $C_{1-2}$. $R^1$ may be $C_1$. $R^1$ may be $C_{2-10}$. $R^1$ may be $C_{2-3}$. $R^1$ may be $C_{2-4}$. $R^1$ may be $C_{2-5}$. $R^1$ may be $C_{2-6}$. $R^1$ may be $C_{2-7}$. $R^1$ may be $C_{2-8}$. $R^1$ may be $C_{2-9}$. $R^1$ may be $C_{2-10}$. $R^1$ may be $C_{2-11}$. $R^1$ may be $C_{2-12}$. $R^1$ may be $C_{2-13}$. $R^1$ may be $C_{2-14}$. $R^1$ may be $C_{2-15}$. $R^1$ may be $C_{2-16}$. $R^1$ may be $C_{2-17}$. $R^1$ may be $C_{2-18}$. $R^1$ may be $C_{2-19}$. $R^1$ may be $C_{2-20}$. $R^1$ may be $C_{3-10}$. $R^1$ may be $C_{4-10}$. $R^1$ may be $C_{5-10}$. $R^1$ may be $C_{6-10}$. $R^1$ may be $C_{7-10}$. $R^1$ may be $C_{8-10}$.

$R^1$ may be $C_{9-10}$. Alternatively, $R^1$ may be optionally substituted. The optional substituent may be selected from one or more of the group including of: oxo, OH, F, Cl, Br, I, $NH_2$, CN, SH, $SO_3H$ and $NO_2$, and zero to ten backbone carbons of the optionally substituted alkyl group may be optionally and independently substituted with O, N or S. T may be COOH. T may be COOEt. T may be COOPr. T may be COOBu. T may be COOMe. $R^1$ may be linear. $R^1$ may be branched. $R^1$ may be cyclic. $R^1$ may be saturated. $R^1$ may be unsaturated.

Z may be F or Cl. D may be F or Cl. Z may be F. D may be F. Z may be Cl. D may be Cl. Z may be F and D may be F or Cl. Z may be Cl and D may be F or Cl. Z may be Cl and D may be Cl. Z may be F and D may be Cl. Z may be F and D may be F. Z may be F and D may be F or Cl. Z may be F or Cl and D may be F. Z may be F or Cl and D may be Cl.

X may be $NH_2$, $NHC(NH)NH_2$, $NHCH_3$, $NHCH_2CH_3$, $NHCH_2CH_2CH_3$, $NHCH_2CH_2CH_2CH_3$, or $NHC(CH_3)CH_3$. X may be $NH_2$. X may be $NHC(NH)NH_2$. X may be $NHCH_3$. X may be $NHCH_2CH_3$. X may be $NHCH_2CH_2CH_3$. X may be $NHCH_2CH_2CH_2CH_3$. X may be $NHC(CH_3)CH_3$. X may be $NH_2$, or $NHC(NH)NH_2$. X may be $NH_2$, $NHC(NH)NH_2$, or $NHCH_3$. X may be $NH_2$, $NHC(NH)NH_2$, or $NHC(CH_3)CH_3$.

Q may be OH, OMe, or OAc. Q may be OH, or OAc. Q may be OAc. Q may be OH. Q may be OMe. Q may be OH, or OMe, or OAc. Q may be OMe, or OAc.

E may be OH, OMe, or OAc. E may be OH, or OAc. E may be OAc. E may be OH. E may be OMe. E may be OH, or OMe, or OAc. E may be OMe, or OAc.

A may be OH, OMe, or OAc. A may be OH, or OAc. A may be OAc. A may be OH. A may be OMe. A may be OH, or OMe, or OAc. A may be OMe, or OAc.

BRIEF DESCRIPTION OF THE DRAWINGS

The invention will now be described in greater detail with reference to the accompanying diagrams.

(FIG. 1A) the mechanism of action of the 2,3-difluorosialic acids (DFSAs); (FIG. 1B) the X-ray crystallographic structure of the active site of an NA trapped as its 3-fluoro(eq)-4-guanidino-sialyl-enzyme intermediate (contacts ≤3 Å are shown with dashed lines; and (FIG. 1C) a diagram of the interactions (≤3 Å; red dashed lines) with the sugar in the covalently inhibited NA.

FIG. 4B shows the dose dependent efficacy of FeqGuDFSA (1-10 mg/kg/d) and zanamivir. FeqGuDFSA was partly (20%) effective at protecting animals at 3 mg/kg/d ((*) Mantel Cox p=0.03), whereas a 10 mg/kg/d dose was 100% effective (dotted line, (***) Mantel Cox p<0.001).

DETAILED DESCRIPTION

Figure 1A:
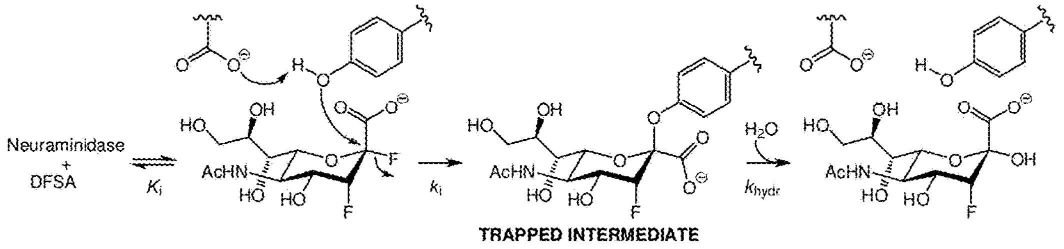
FIGS. 1A-1C include a schematic depiction of the mechanism of action of DFSAs and the X-ray structure of inhibited enzyme, including the following.

As used herein, the phrase "$C_{x-y}$ alkyl" or "$C_x$-$C_y$ alkyl" is used as it is normally understood to a person of skill in the art and often refers to a chemical entity that has a carbon skeleton or main carbon chain comprising a number from x to y (with all individual integers within the range included, including integers x and y) of carbon atoms. For example a "$C_{1-10}$ alkyl" is a chemical entity that has 1, 2, 3, 4, 5, 6, 7, 8, 9 or 10 carbon atom(s) in its carbon skeleton or main chain. Alternatively, for example a "$C_{1-20}$ alkyl" is a chemical entity that has 1, 2, 3, 4, 5, 6, 7, 8, 9, 10, 11, 12, 13, 14, 15, 16, 17, 18, 19, or 20 carbon atom(s) in its carbon skeleton or main chain.

As used herein, the term "branched" is used as it is normally understood to a person of skill in the art and often refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl are tert-butyl and isopropyl.

As used herein, the term "unbranched" is used as it is normally understood to a person of skill in the art and often refers to a chemical entity that comprises a skeleton or main chain that does not split off into more that one contiguous chain. Non-limiting examples of unbranched alkyls are methyl, ethyl, n-propyl, and n-butyl.

As used herein, the term "substituted" is used as it is normally understood to a person of skill in the art and often refers to a chemical entity that has one chemical group replaced with a different chemical group that contains one or more heteroatoms. Unless otherwise specified, a substituted alkyl is an alkyl in which one or more hydrogen atom(s) is/are replaced with one or more atom(s) that is/are not hydrogen(s). For example, chloromethyl is a non-limiting example of a substituted alkyl, more particularly an example of a substituted methyl Aminoethyl is another non-limiting example of a substituted alkyl, more particularly it is a substituted ethyl. The functional groups described herein may be substituted with, for example, and without limitation, 1, 2, 3, 4, 5, 6, 7, 8, 9 or 10 substituents.

As used herein, the term "unsubstituted" is used as it is normally understood to a person of skill in the art and often refers to a chemical entity that is a hydrocarbon and/or does not contain a heteroatom. Non-limiting examples of unsubstituted alkyls include methyl, ethyl, tert-butyl, and pentyl.

As used herein, the term "saturated" when referring to a chemical entity is used as it is normally understood to a person of skill in the art and often refers to a chemical entity that comprises only single bonds. Non-limiting examples of saturated chemical entities include ethane, tert-butyl, and $N^+H_3$.

As used herein the term "halogenated" is used as it would normally be understood to a person of skill in the art and refers to a moiety or chemical entity in which a hydrogen atom is replaced with a halogen atom such as chlorine, fluorine, iodine or bromine. For example, a fluorinated side chain refers to a side chain wherein one or more hydrogen atoms is replaced with one or more fluorine atoms.

Non-limiting examples of saturated $C_1$-$C_{10}$ alkyl may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, 1-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl and t-decyl. Non-limiting examples of $C_2$-$C_{10}$ alkenyl may include vinyl, allyl, isopropenyl, 1-propene-2-yl, 1-butene-1-yl, 1-butene-2-yl, 1-butene-3-yl, 2-butene-1-yl, 2-butene-2-yl, octenyl and decenyl. Non-limiting examples of $C_2$-$C_{10}$ alkynyl may include ethynyl, propynyl, butynyl, pentynyl, hexynyl, heptynyl, octynyl, nonynyl and decynyl. Saturated $C_1$-$C_{10}$ alkyl, $C_2$-$C_{10}$ alkenyl or $C_2$-$C_{10}$ alkynyl may be, for example, and without limitation, interrupted by one or more heteroatoms which are independently nitrogen, sulfur or oxygen.

The embodiments involving the formulae as described herein include all possible stereochemical alternatives except where expressly excluded, including those illustrated or described herein.

In some embodiments, the compounds as described herein or acceptable salts thereof above may be used for systemic treatment or prophylaxis of a viral infection. In some embodiments, the compounds as described herein or acceptable salts thereof above may be used in the preparation of a medicament or a composition for systemic treatment or prophylaxis of a viral infection. In some embodiments, methods of systemically treating any of the infections described herein are also provided. Some embodiments, make use of compositions comprising a compound described herein and a pharmaceutically acceptable excipient or carrier. In some embodiments, the viral infection is caused, at least in part, by an influenza virus. Methods of treating any of the indications described herein are also provided. Such methods may include administering a compound as described herein or a composition comprising a compound as described herein, or an effective amount of a compound as described herein or composition comprising a compound as described herein to a subject in need thereof.

Compounds as described herein may be in the free form or in the form of a salt thereof. In some embodiments, compounds as described herein may be in the form of a pharmaceutically acceptable salt, which are known in the art (Berge et al., *J. Pharm. Sci.* (1977) 66:1). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid, an inorganic acid, an organic base or an inorganic base, or by anion exchange or cation exchange from other salts. Those skilled in the art will appreciate that preparation of salts may occur in situ during isolation and/or purification of the compounds or preparation of salts may occur by separately reacting an isolated and/or purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association with the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and/or amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein may include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience unless specifically excluded.

In some embodiments, pharmaceutical compositions in accordance with this invention may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, oral, topical administration, lavage, or other modes suitable for the selected treatment. Suitable carriers, excipients or diluents include those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy* by Alfonso Gennaro, $20^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. The formulations may be specifically prepared for intranasal delivery. For example, nasal inhalation.

Compounds or pharmaceutical compositions in accordance with this invention or for use in this invention may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition as described herein includes a therapeutically effective amount or a prophylactically effective amount. A "therapeutically effective amount" refers to an amount effective, at dosages and for periods of time necessary, to achieve the desired therapeutic result, such as reduced viral load, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as less severe infection or delayed or no onset, increased life span, increased life expectancy or prevention of the progression of infection. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In some embodiments, compounds and all different forms thereof as described herein may be used, for example, and without limitation, in combination with other treatment methods.

In general, compounds described herein should be used without causing substantial toxicity. Toxicity of the compounds of the invention can be determined using standard techniques, for example, by testing in cell cultures or experimental animals and determining the therapeutic index (evaluate the animals for acute and chronic signs of injury after administration of the drug and determining the maximum tolerated dose (MTD) as for example the dose at which no adverse effects are observed or at which only tolerable effects are observed, and then be compared to the effective dose and ratio of MTD to effective dose becomes the therapeutic index). In some circumstances, however, such as in severe disease conditions, it may be necessary to administer substantial excesses of the compositions. Some compounds described herein may be toxic at some concentrations. Titration studies may be used to determine toxic and non-toxic concentrations. Toxicity may be evaluated by examining a particular compound's or composition's specificity across cell lines. Animal studies may be used to provide an indication if the compound has any effects on other tissues.

Compounds as described herein may be administered to a subject. As used herein, a "subject" may be a human, non-human primate, rat, mouse, cow, horse, pig, sheep, goat, dog, cat, etc. The subject may have, be at risk for having, be suspected of having or being at risk for having an infection, such as a viral infection. In particular, the infection may be facilitated by or mediated by or assited by a neuraminidase. Diagnostic methods for viral infection, such as influenza and the clinical delineation of viral infection, such as influenza are known to those of ordinary skill in the art.

TABLE 1A Comparative test of compounds for neuraminidase modulatory activity.

TABLE 1A

| 2,3-Fluorinated Glycosides having both a 3 equatorial and 3 axial Fluorines (DFSA and derivatives thereof) | |
|---|---|
| Compound | Structure |
| DFSA | 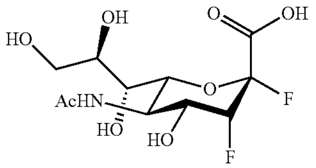 |
| FaxAmDFSA (Compound $4NH_23Fax$) | 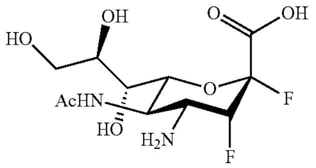 |
| 4-G 3 F equatorial diFSA (4-G 3Feq diFSA) (FeqGuDFSA) (Compound 4G3Feq) | 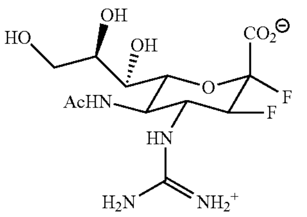 |
| | 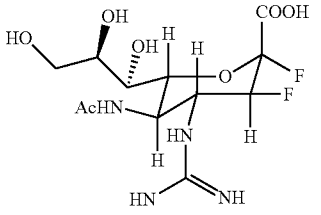 (alternative representation) |
| $4-NH_2$ 3 F equatorial diF SA ($2F3F4NH_2$) (FeqAmDFSA) (Compound $4NH_23Feq$) | 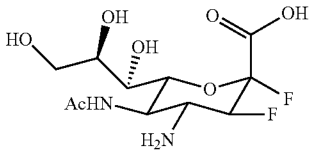 [SMILES: CC(=O)NC1C(N)C(F)C(F)(C(=O)O)OC1[C@H](O)[C@H](O)CO] |
| 4-G diF SA (FaxGuDFSA) (Compound 4G3Fax) | 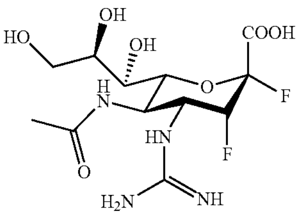 |

TABLE 1B Known anti-viral compounds for comparative activity testing.

TABLE 1B

| Known Anti-viral Compounds | |
|---|---|
| Compound | Structure |
| Zanamivir (Cass # 139110-80-8) | 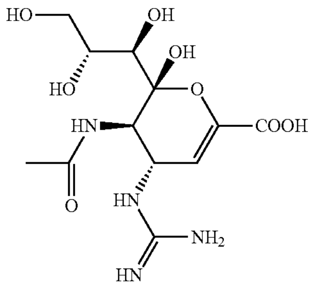 [SMILES: CC(=O)N[C@@H]1[C@@H](NC(=N)N)C=C(C(=O)O)O[C@@]1(O)[C@H](O)[C@H](O)CO] |
| Peramivir (Cass # 229614-55-5) | 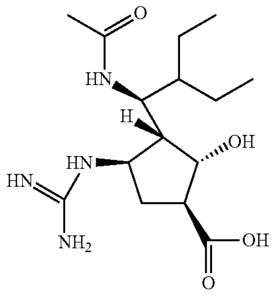 [SMILES: CCC(CC)[C@H](NC(C)=O)[C@@H]1[C@H](O)[C@@H](C(=O)O)C[C@H]1NC(=N)N] |
| Oseltamivir (Cass # 196618-13-0) | 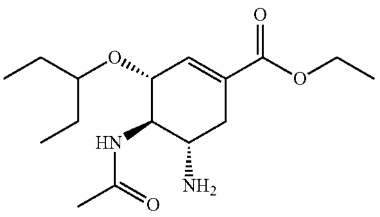 [SMILES: CCOC(=O)C1=C[C@@H](OC(CC)CC)[C@H](NC(C)=O)[C@@H](N)C1] |

TABLE 2 New compounds having surprisingly good neuraminidase modulatory properties.

TABLE 2

| Equatorial 2,3-Fluorinated Glycosides with Neuraminidase Modulatory Activity | |
|---|---|
| Compound | Structure |
| FeqGuDFSA | 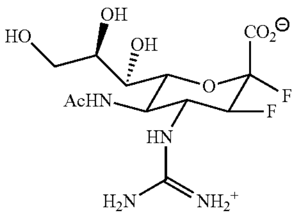 (alternative representation) |

TABLE 2-continued

Equatorial 2,3-Fluorinated Glycosides with Neuraminidase Modulatory Activity

| Compound | Structure |
|---|---|
| | 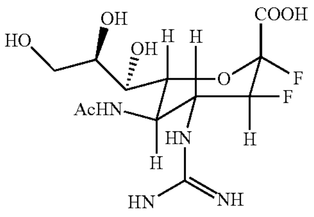 [SMILES: CC(=O)NC1C([C@H](O)[C@H](O)CO)C2OC(F)(C(=O)O)C(F)C12NC(=N)N] |
| FeqAmDFSA | 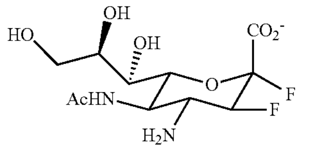 |
| | 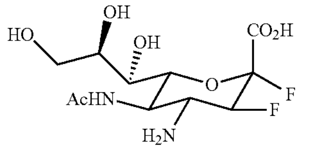 (alternative representation) |
| | 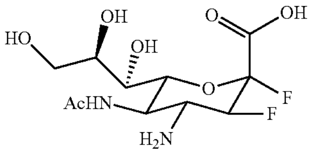 (alternative representation) |

Compounds described herein may also be used in assays and for research purposes. Compounds for use in the present methods may be synthesized using the methods described herein.

Various alternative embodiments and examples are described herein. These embodiments and examples are illustrative and should not be construed as limiting the scope of the invention.

General Methodologies

Synthesis

All chemicals were of analytical grade purchased from the Sigma-Aldrich company, unless otherwise stated. All solvents were BOC standard grade and distilled before use. Dichloromethane was distilled from calcium hydride. Methanol was distilled from magnesium. N,N-dimethylformamide and DIPEA were dried and stored over 4 Å molecular sieves. Analytical thin-layer chromatography (TLC) was performed on aluminum-backed sheets of Silica Gel $60F_{254}$ (E. Merck) of thickness 0.2 mm. The plates were visualized using UV light (254 nm) and/or by exposure to 10% ammonium molybdate (2 M in $H_2SO_4$) followed by charring. Flash column chromatography was carried out using Merck Kieselgel 60 (230-400 mesh). Proton and carbon NMR spectra were recorded on Bruker Avance 400 inv, 400 dir and 300 Fourier Transform spectrometers fitted with 5 mm BBI-Z probes. Fluorine NMR spectra were recorded on a Bruker Avance 300 fitted with a 5 mm QNP probe. All spectra were recorded using an internal deuterium lock and are referenced internally using the residual solvent peak. Carbon and proton chemical shifts are quoted in parts per million (ppm) downfield of tetramethylsilane, fluorine chemical shifts are quoted downfield of trifluoroacetic acid. Coupling constants (J) are given in Hertz (Hz) and are quoted to the nearest 0.5 Hz. Carbon NMR spectra were performed with broadband proton decoupling and were recorded with DEPT. $^1$H-NMR experiments performed in $D_2O$ solvent were recorded with a water suppression protocol. Mass spectra were recorded on a Waters/Micromass LCT using electrospray ionization (ESI) and recorded using the Time-Of-Flight (TOF) method using methanol as solvent.

General methodologies for chemical preparation of 3' equatorial compounds of Formula I are described in the following non-limiting exemplary schemes. Furthermore, additional modifications to the below exemplary schemes and alternative syntheses as described in PCT/CA2010/001063.

Scheme 1

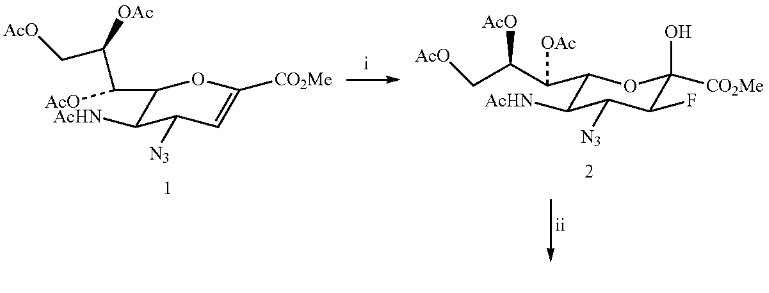

-continued

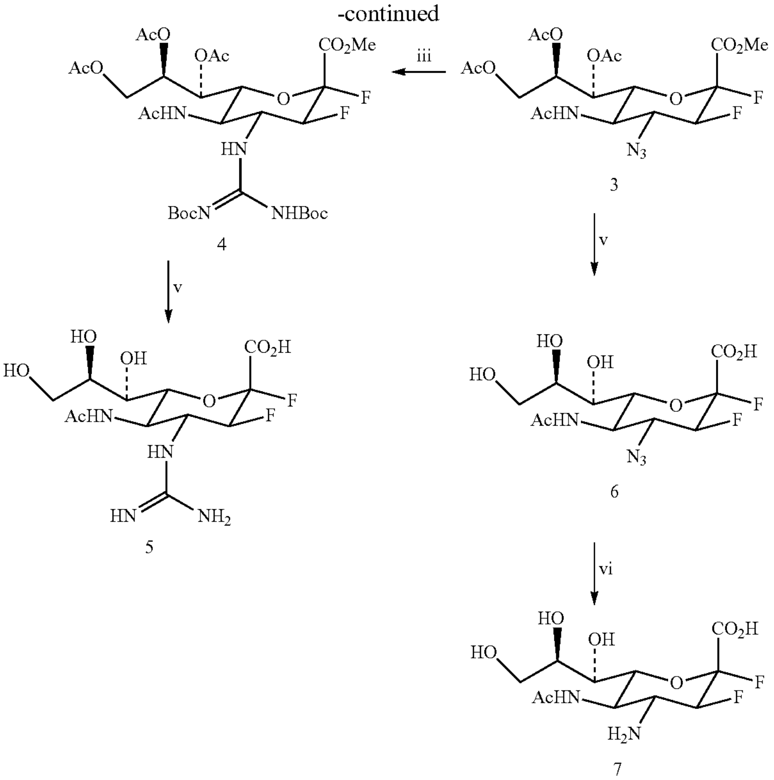

3
4
5
6
7 i. $CH_3NO_2$, $H_2O$, Selectfluor, rt, 18%. ii. DCM, DAST, −40° C., 91%. iii. EtOAc, Pd/C (10%), DIPEA, N, N'-di-Boc-N"-trifluoromethanesulfonylguanidine, rt, 54%. iv. MeOH, NaOMe; TFA, rt, 70%. v. MeOH, NaOMe; $H_2O$, rt, 96%. vi. MeOH, Pd/C, rt, 100%.

Compounds of Formula I having modifications at C1, may be prepared by the chemical methodologies described in the following non-limiting exemplary scheme.

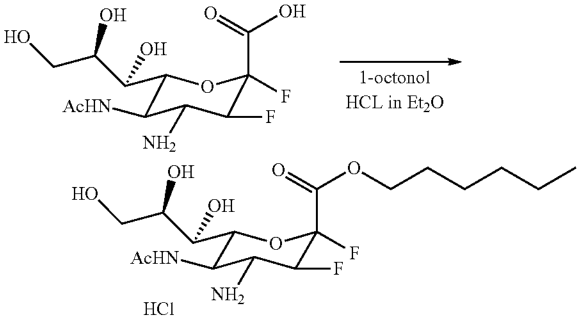

It will be appreciated by a person of skill in the art, that variations in the alkyl chain length may be achieved by substituting 1-octanol (C8—having 8 carbons) for an alternative alcohol. For example, 1-octanol in the above scheme may be substituted for an alternative primary alcohol, which may, for example, be selected from one or more of the following: Propan-1-ol (C3); Butanol (C4); 1-Pentanol (C5); 1-Hexanol (C6); 1-Heptanol (C7); 1-Nonanol (C9); 1-Decanol (C10); Undecanol (C11); Dodecanol (C12); 1-Tetradecanol (C14); Cetyl alcohol (C16); Stearyl alcohol (C18); and Arachidyl alcohol (C20). Similarly, it will be appreciated that an alternative substrate for this reaction may be chosen. For example, instead of the $4NH_2$ (compound 7) the 4Gu compound (compound 5), or etc. may be substituted.

Alternatively, compounds of Formula I having modifications at C1, may be prepared by the chemical methodologies described in the following non-limiting exemplary scheme. For example, the below exemplary scheme adds an ethyl group at C1 ($R^1$). It will be appreciated by a person of skill in the art, that variations in the salt produced may be achieved by substituting an alternative acid and that the length of the alkyl group at C1 may be adjusted by substituting an alternative alcohol as set out above.

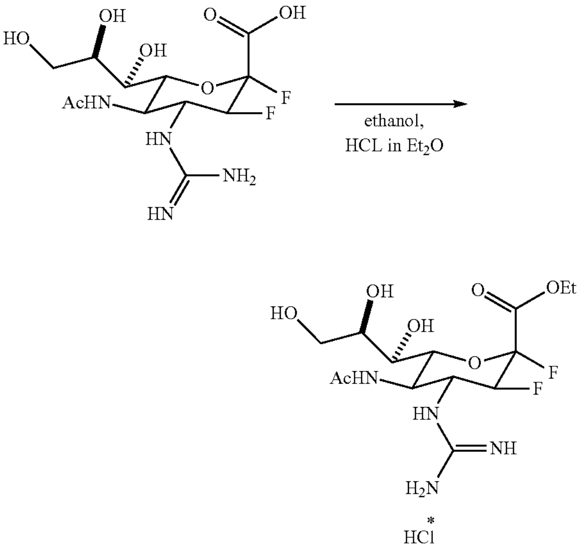

Syntheses and Characterizations

Methyl 5-acetamido-7, 8, 9-tri-O-acetyl-4-azido-4, 5-dideoxy-3β-fluoro-D-erythro-L-gluco-nonulopyranosonate (2)

"Methyl 5-acetamido-7,8,9-tri-O-acetyl-4-azido-3,4,5-trideoxy-3β-fluoro-D-erythro-L-glucononulopyranosonate": A suspension of 1 (11.1 g, 24.3 mmol), nitromethane (95 mL), water (16 mL) and Selectfluor (34.5 g, 97.5 mmol, 4 equiv.) was stirred for 7 days at room temperature. (The reaction may be monitored for completion by UV on TLC, because only the starting material is detected under short UV. The reaction is considered complete upon disappearance of the UV active compound.). The reaction was quenched with saturated $NaHCO_3$ (100 mL), extracted with EtOAc (4×200 mL). The organic phase was washed with saturated $NaHCO_3$ (300 mL) and brine (300 mL), dried over $MgSO_4$. After evaporation, the resulting residue was purified by flash column chromatography ($CHCl_3$/Acetone/EtOAc=5/1/1) to give the desired compound 2 as a white solid (2.14 g, 18%). $^1$H NMR (400 MHz, $CDCl_3$): δ 5.73 (d, 1H, J 9.2 Hz, NHAc), 5.30 (dd, 1H, $J_{7,8}$6.7 Hz, H-7), 5.22 (m, 1H, H-8), 4.74 (dd, 1H, $J_{3,4}$ 9.6 Hz, $J_{H3,F3}$49.0 Hz, H-3), 4.66 (s, 1H, OH), 4.40 (dd, 1H, $J_{6,7}$1.8 Hz, $J_{5,6}$ 10.5 Hz, H-6), 4.37 (dd, 1H, $J_{8,9a}$ 2.1 Hz, H-9a), 4.20 (m, 1H, H-4), 4.04 (dd, 1H, $J_{8,9b}$ 6.3 Hz, $J_{9a,9b}$ 12.4 Hz, H-9b), 3.96 (s, 3H, $OCH_3$), 3.77 (m, 1H, H-5), 2.15 (s, 3H, $CH_3CO$), 2.11 (s, 3H, $CH_3CO$), 2.04 (s, 3H, $CH_3CO$), 2.03 (s, 3H, $CH_3CO$). $^{13}$C NMR (75 MHz, $CDCl_3$): δ 170.9, 170.7, 170.6 (2C), 167.8, 93.3 (d, $J_{C2}$, $F_3$ 21.8 Hz, C-2), 89.2 (d, $J_{C3,\ F3}$ 193.8 Hz, C-3), 70.5, 69.6, 67.7, 62.6, 62.0 (d, $J_{C4,\ F3}$ 17.2 Hz, C-4), 54.55, 49.9 (d, J $C_5$, $F_3$ 6.0 Hz, C-5), 23.6, 21.2, 21.0, 20.9. $^{19}$F NMR (282 MHz, $CDCl_3$): δ −195.46 (s, F-2 eq). ESI-MS: 515.3 $[(M+Na)^{+]}$.

Methyl 5-acetamido-7, 8, 9-tri-O-acetyl-4-azido-2, 4, 5-trideoxy-2α, 3β-difluoro-α-D-erythro-L-gluco-nonulopyranosonate (3)

"Methyl 5-acetamido-7,8,9-tri-O-acetyl-4-azido-3,4,5-trideoxy-2α 3β-difluoro-α-D-erythro-L-glucononulopyranosonate": To a suspension of 2 (0.62 g, 1.3 mmol) in dry DCM (18 mL) was added dropwise DAST (0.18 mL, 1.4 mmol, 1.1 equiv) with stirring under $N_2$ at −40° C. After addition, the reaction mixture was stirred for 0.5 h at −40° C., and then gradually warmed up to −10° C. The reaction was quenched with saturated $NaHCO_3$, diluted with DCM (50 mL) and washed with brine (30 mL). The water phase was extracted again with EtOAc (2×50 mL) and washed with brine (50 mL). The combined organic phase was dried over $MgSO_4$. After evaporation, the resulting residue was purified by flash column chromatography (DCM/Acetone=8/1) to give product 3 as a white solid (0.566 g, 91%). $^1$H NMR (400 MHz, $CDCl_3$): δ 5.59 (d, 1H, J 9.0 Hz, NHAc), 5.32 (m, 1H, H-8), 5.24 (dt, 1H, $J_{7,8}$8.5 Hz, H-7), 4.70 (dd, 1H, $J_{5,6}$10.7 Hz, $J_{6,7}$1.6 Hz, H-6), 4.66 (ddd, 1H, $J_{4,5}$10.7 Hz, $J_{H4,F3}$ 20.2 Hz, H-4), 4.47 (ddd, 1H, $J_{3,4}$ 9.3 Hz, $J_{H3,F3}$ 48.6 Hz, $J_{H3,F2}$ 14.5 Hz, H-3), 4.25 (dd, 1H, $J_{8,9a}$ 2.6 Hz, H-9a), 4.13 (dd, 1H, $J_{8,9b}$ 5.2 Hz, $J_{9a,9b}$ 12.5 Hz, H-9b), 3.91 (s, 3H, $OCH_3$), 3.62 (m, 1H, H-5), 2.14 (s, 3H, $CH_3CO$), 2.08 (s, 3H, $CH_3CO$), 2.05 (s, 3H, $CH_3CO$), 2.04 (s, 3H, $CH_3CO$). $^{13}$C NMR (75 MHz, $CDCl_3$): δ 171.0, 170.7, 170.5, 169.7, 165.3 (d, $J_{C2,F2}$ 32.8 Hz, C-1), 105.5 (dd, $J_{C2,\ F2}$ 229.1 Hz, $J_{C2,F3}$ 27.2 Hz, C-2), 92.0 (dd, $J_{C3,F3}$ 192.2 Hz, $J_{C3,F2}$29.0 Hz, C-3), 72.9, 68.9, 67.0, 62.2, 61.8 (dd, $J_{C4,F3}$ 18.1 Hz, $J_{C4,F2}$ 8.4 Hz, C-4), 53.7, 49.2 (d, $J_{C5,F3}$ 6.9 Hz, C-5), 23.5, 21.0 (2C), 20.9. $^{19}$F NMR (282 MHz, $CDCl_3$): δ −119.4 (d, $J_{F2,F3}$ 12.7 Hz, F-2 eq), −197.5 (d, F-3 eq). ESI-MS: 517.2 $[(M+Na)^+]$.

Methyl 5-acetamido-7, 8, 9-tri-O-acetyl-4-[(N',N"-di-tert-butoxycarbonyl) guanidine]-2, 4, 5-trideoxy-2α, 3β-difluoro-α-D-erythro-L-gluco-nonulpyranosonate (4)

"Methyl 5-acetamido-7,8,9-tri-O-acetyl-4-[(N',N"-di-tert-butoxycarbonyl) guanidine]-3,4,5-trideoxy-2α,3β-difluoro-α-D-erythro-L-glucononulpyranosonate": A mixture of 3 (260 mg, 0.53 mmol), EtOAc (10 mL), Pd/C (10%, 60 mg), N, N'-di-Boc-N"-trifluoromethanesulfonylguanidine (350 mg, 0.9 mmol, 1.7 equiv) and DIPEA (0.2 mL) was placed under vacuum and then filled with hydrogen three times, and the mixture was stirred under a $H_2$ atmosphere for 24 h at room temperature. The reaction mixture was filtered through a short pad of Celite and washed with EtOAc. After evaporation, the resulting residue was purified by flash column chromatography (DCM/Acetone=15/1) to give the product 4 as a white solid (0.311 g, 83%). $^1$H NMR (400 MHz, $CDCl_3$): δ 11.37 (s, 1H, NHBoc), 8.67 (d, 1H, J 7.8 Hz, NHGuanidine), 6.45 (d, 1H, J 9.0 Hz, NHAc), 5.32 (m, 1H, H-8), 5.25 (brd, 1H, $J_{7,8}$7.7 Hz, H-7), 4.90 (m, 1H, H-4), 4.71 (ddd, 1H, $J_{3,4}$ 8.8 Hz, $J_{H3,F3}$48.5 Hz, $J_{H3,F2}$12.5 Hz, H-3), 4.50 (brd, 1H, H-6), 4.32 (dd, 1H, $J_{8,9a}$ 2.6 Hz, H-9a), 4.28 (m, 1H, H-5), 4.07 (dd, 1H, $J_{8,9b}$ 6.2 Hz, $J_{9a,9b}$ 12.4 Hz, H-9b), 3.90 (s, 3H, $OCH_3$), 2.15 (s, 3H, $CH_3CO$), 2.09 (s, 3H, $CH_3CO$), 2.04 (s, 3H, $CH_3CO$), 1.88 (s, 3H, $CH_3CO$), 0.99 (s, 18H, 2×Boc). $^{13}$C NMR (75 MHz, $CDCl_3$): δ 171.2, 171.1, 170.2, 169.8, 165.1 (d, $J_{C2,F2}$32.8 Hz, C-1), 162.7, 157.5, 152.9, 105.7 (dd, $J_{C2,FC2}$ 226.7 Hz, $J_{C2,F3}$ 27.8 Hz, C-2), 90.4 (dd, $J_{C3,F3}$ 191.8 Hz, $J_{c3,F2}$31.9 Hz, C-3), 84.4, 80.3, 74.7, 69.3, 67.2, 62.5, 53.7, 52.8 (dd, $J_{C4,F3}$ 20.3 Hz, $J_{C4,F2}$6.2 Hz, C-4), 49.0 (d, $J_{C5,F3}$5.0 Hz, C-5), 28.3 (3C), 28.1 93C), 23.1, 21.0 (2C), 20.9. $^{19}$F NMR (282 MHz, $CDCl_3$): δ −115.6 (d, $J_{F2,F3}$ 11.3 Hz, F-2 eq), −195.8 (d, F-3 eq). ESI-MS: 733.4 $[(M+Na)^+]$.

5-Acetamido-2, 4, 5-trideoxy-2α, 3β-difluoro-4-guanidino-α-D-erythro-L-gluco-nonulopyranosonate (5)

"5-Acetamido-3,4,5-trideoxy-2α,3β-difluoro-4-guanidino-α-D-erythro-L-gluco-nonulopyranosonate": To a solution of 4 (71 mg, 0.1 mmol) in dry methanol (6 mL) was added sodium methylate solution (5.4 M, 0.1 mL) under $N_2$, and the reaction mixture was stirred overnight at room temperature. The reaction was neutralized with Amberlite (IR-120), filtered and washed with methanol, evaporated to give a residue. The resulting residue was dissolved into TFA (1 mL) and stirred for 2 h at room temperature, evaporated and co-evaporated with toluene three times. The crude product was purified by flash column chromatography (EtOAc/MeOH/$H_2O$=7/2/1) to give compound 5 as a white solid (26 mg, 92%). $^1$H NMR (400 MHz, $D_2O$): δ 4.71 (ddd, 1H, $J_{3,4}$ 8.9 Hz, $J_{H3,F3}$ 48.8 Hz, $J_{H3,F2}$ 13.4 Hz, H-3), 4.56 (ddd, 1H, $J_{H4,F3}$ 19.0 Hz, H-4), 4.49 (brd, 1H, H-6), 4.36 (t, 1H, $J_{4,5}$=$J_{5,6}$10.5 Hz, H-5), 3.84 (dd, 1H, $J_{8,9a}$ 2.6 Hz, H-9a), 3.79 (m, 1H, H-8), 3.62 (dd, 1H, $J_{8,9b}$ 6.0 Hz, $J_{9a,9b}$ 11.5 Hz, H-9b), 3.56 (brd, 1H, $J_{7,8}$9.1 Hz, H-7). $^{13}$C NMR (75 MHz, $D_2O$): δ 174.6, 169.6 (d, $J_{C2,F2}$ 30.8 Hz, C-1), 157.6, 106.8 (dd, $J_{C2,\ F2}$222.1 Hz, $J_{c2,F3}$ 27.8 Hz, C-2), 91.5 (dd, $J_{C3,F3}$ 188.1 Hz, $J_{C3,F2}$ 31.5 Hz, C-3), 73.5, 69.9, 67.9, 63.2, 55.7 (dd, $J_{C4,F3}$ 18.8 Hz, $J_{C4,F2}$ 8.2 Hz, C-4), 48.4 (d, $J_{C5,F3}$ 6.4

Hz, C-5), 21.9. $^{19}F$ NMR (282 MHz, $D_2O$): 5-112.7 (d, $J_{F2,F3}$ 12.7 Hz, F-2 eq), −199.2 (d, F-3 eq). ESI-MS: 369.4 $[(M-H)^-]$.

5-Acetamido-2, 4, 5-trideoxy-4-azido-2α, 3β-difluoro-α-D-erythro-L-gluco-nonulo-pyranosonate (6)

"5-Acetamido-3,4,5-trideoxy-4-azido-2α,3β-difluoro-α-D-erythro-L-glucononulo-pyranosonate": To a solution of 3 (50 mg, 0.1 mmol) in dry methanol (5 mL) was added sodium methylate solution (5.4 M, 50 μL) under $N_2$, and the reaction mixture was stirred for 2 h at room temperature. To the reaction mixture was added a couple drops of water, and stirred for another an hour at room temperature. The reaction was neutralized with Amberlite (IR-120), filtered and washed with methanol, and evaporated to give a residue. The resulting residue was purified by flash column chromatography ($EtOAc/MeOH/H_2O$=12/2/1) to give product 6 as a white solid (34 mg, 96%). $^1H$ NMR (400 MHz, $CD_3OD$): δ 4.69 (ddd, 1H, $J_{H4,F3}$ 19.7 Hz, H-4), 4.43 (ddd, 1H, $J_{3,4}$ 9.0 Hz, $J_{H3,F3}$50.0 Hz, $J_{H3,F2}$13.5 Hz, H-3), 4.39 (brd, 1H, H-6), 4.11 (t, 1H, $J_{4,5}$=$J_{5,6}$ 10.6 Hz, H-5), 3.79 (dd, 1H, $J_{8,9a}$ 2.8 Hz, H-9a), 3.77 (m, 1H, H-8), 3.64 (dd, 1H, $J_{8,9b}$ 5.2 Hz, $J_{9a,9b}$ 11.3 Hz, H-9b), 3.49 (brd, 1H, $J_{7,8}$9.1 Hz, H-7). $^{13}C$ NMR (75 MHz, $CD_3OD$): δ 173.2, 169.0 (d, $J_{C2,F2}$ 45.4 Hz, C-1), 106.5 (dd, $J_{C2,F2}$, 222.6 Hz, $J_{C2,F3}$28.0 Hz, C-2), 92.6 (dd, $J_{C3,F3}$ 188.8 Hz, $J_{c3,F2}$30.3 Hz, C-3), 73.9, 70.4, 68.4, 63.4, 63.1 (dd, $J_{C4,F3}$ 24.8 Hz, $J_{C4,F2}$ 8.0 Hz, C-4), 49.1 (d, $J_{C5,F3}$ 6.3 Hz, C-5), 21.4. $^{19}F$ NMR (282 MHz, $CD_3OD$): 5-115.7 (d, $J_{F2,F3}$ 11.3 Hz, F-2 eq), −199.6 (d, F-3 eq). ESI-MS: 353.2 $[(M-H)^-]$.

5-Acetamido-2, 4, 5-trideoxy-4-amino-2α, 3β-difluoro-α-D-erythro-L-gluco-nonulo-pyranosonate (7)

"5-Acetamido-3,4,5-trideoxy-4-amino-2α,3β-difluoro-α-D-erythro-L-glucononulo-pyranosonate" A suspension of 6 (39 mg, 0.11 mmol) and Pd/C (10%, 12 mg) in dry methanol (8 mL) was vacuumed and filled with hydrogen for three times, and stirred overnight under $H_2$ atmosphere at room temperature. The reaction mixture was filtered through a short pad of Celite and washed with methanol. The organic solvent was evaporated to give a solid. The solid was dissolved in distilled water and filtered with MILLEX-GP filter unit (pore size: 0.22 μm), and then lyophilized to give compound 7 as a white solid (36 mg, 100%). $^1H$ NMR (400 MHz, $D_2O$): δ 4.83 (ddd, 1H, $J_{3,4}$ 9.1 Hz, $J_{H3,F3}$49.6 Hz, $J_{H3,F2}$13.2 Hz, H-3), 4.46~4.28 (m, 3H, H-4, H-5 & H-6), 3.84 (dd, 1H, $J_{8,9a}$. 2.5 Hz, H-9a), 3.79 (m, 1H, H-8), 3.62 (dd, 1H, $J_{8,9b}$ 6.0 Hz, $J_{9a,9b}$ 11.7 Hz, H-9b), 3.54 (brd, 1H, $J_{7,8}$9.0 Hz, H-7). $^{13}C$ NMR (100 MHz, $D_2O$): δ 175.1, 169.2 (d, $J_{C2,F2}$ 30.0 Hz, C-1), 106.4 (dd, $J_{C2,F2}$222.0 Hz, $J_{C2,F3}$ 28.0 Hz, C-2), 90.1 (dd, $J_{C3,F3}$ 186.0 Hz, $J_{C3,F2}$ 33.0 Hz, C-3), 73.6, 69.9, 67.7, 63.2, 54.0 (dd, $J_{C4,F3}$ 18.0 Hz, $J_{C4,F2}$7.0 Hz, C-4), 46.9 (d, $J_{C5,F3}$ 6.0 Hz, C-5), 22.2. $^{19}F$ NMR (282 MHz, $D_2O$): δ −113.6 (d, $J_{F2,F3}$ 14.1 Hz, F-2 eq), −199.9 (d, F-3 eq). ESI-MS: 327.3 $[(M-H)^-]$.

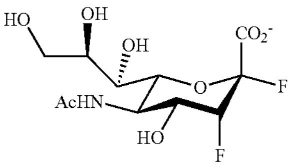

DFSA

-continued

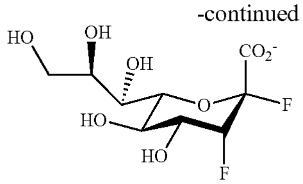

DifluoroKDN

5-Acetamido-5-deoxy-3-fluoro-D-erythro-β-L-manno-2-nonulopyranosonic acid fluoride (DFSA)

DFSA was synthesized according to the procedure of Watts and Withers (A. G. Watts, S. G. Withers, *Can. J. Chem.* 82, 1581 (2004)).

2-Keto-3-deoxy-3-fluoro-D-glycero-β-L-manno-2-nonulosonic acid fluoride (difluoroKDN)

DifluoroKDN was synthesized according to the procedure of Watts et al. (A. G. Watts et al., *J. Biol. Chem.* 281, 4149 (2006)).

Enzyme Kinetics

Measurement of Inactivation and Reactivation Kinetic Parameters

Influenza A Neuraminidase

All experiments were carried out in a 20 mM Tris/50 mM $CaCl_2$ buffer, pH 7.6. Cuvettes had a path length of 1 cm and were used in a Cary 4000 UV/visible spectrophotometer connected to a circulating water bath. The data were analyzed using the program GraFit 4.0 (Erithacus software) (R. Leatherbarrow, *Erithacus Software Ltd.*, 4*th Edition, Staines*, UK, (1990)). The viral stock solution was prepared by adding 300 μL of buffer, 50 μL 1% BSA and 50 μL 4% Triton X-100 to 100 μL of virus solution that had been treated with NP-40 to kill any viral infectivity. Time-dependent inactivations were performed by pre-incubating the viral stock (60 μL) at 30° C. in the presence of several concentrations of inactivator (ranging from 0.05 μM to 10 μM), buffer and 1% BSA (20 μL), in a total volume of 200 μL. Residual enzyme activity was determined at appropriate time intervals by the addition of an aliquot of the inactivation mixture (30 μL) to an assay solution containing 0.75 mM 4-trifluoromethylumbelliferyl sialic acid ($CF_3MUSA$). Kinetic parameters were determined by measuring the initial linear increase in absorbance at 400 nm. The initial rates at each time point were plotted as a function of time to obtain time-dependent exponential decay curves from which $k_{i\ obs}$ could be obtained for each inactivator concentration using the equation:

$$(rate)_t=(rate)_{t=0}e^{(ki\ obs\ t)}+offset$$

The inactivation rate constant ($k_i$) and the reversible dissociation constant for the inactivator ($K_i$) were determined by fitting data for $k_{i\ obs}$ versus inactivator concentration to the equation:

$$k_{i\ obs}=k_i[I](K_i+[I])$$

In the case where $[I]<<K_i$, a second-order rate constant ($k_i/K_i$) was determined by fitting the data to the equation:

$$k_{i\ obs}=k_i[I]/K_i$$

Time-dependent reactivation parameters were determined as follows. Inactivated enzyme solution (200 μl) was applied to a Ultrafree® 0.5 Centrifugal Device 50 K filter (Millipore™) at 4° C. to remove excess inactivator. The filter was washed once with 200 μL buffer at 4° C. The eluted enzyme was dissolved with 200 μL buffer. From this solution a 180 μL aliquot was added to a solution of 1% BSA (60 μL) and buffer (360 μL) and incubated at 30° C. Enzyme activity was assayed at time intervals by the addition of an aliquot of eluted enzyme (30 μL) to an assay solution containing 0.75 mM $CF_3$MUSA, at 30° C. First-order rate constants for reactivation ($k_{r,\ hyd}$) were determined by direct fit of the activity versus time data to a first-order equation.

Human Neu2

All experiments were carried out in a 100 mM $Na_2HPO_4$/50 mM Citric acid buffer, pH 5.6. Cuvettes had a path length of 1 cm and were used in a Cary 4000 UV/visible spectrophotometer connected to a circulating water bath. The data were analyzed using the program GraFit 4.0 (Erithacus software) (R. Leatherbarrow, *Erithacus Software Ltd., 4th Edition, Staines*, UK, (1990)). Time-dependent inactivation studies were performed by pre-incubating the enzyme (60 μL) at 27° C. in the presence of 1 mM inactivators (FaxGuDFSA, FeqAmDFSA and FeqGuDFSA), buffer and 0.5% BSA (20 μL), in a total volume of 200 μL. Residual enzyme activity was determined at appropriate time intervals by the addition of an aliquot of the inactivation mixture to an assay buffer solution containing 8 mM 4-trifluoromethylumbelliferyl sialic acid ($CF_3$MUSA). The initial linear increase in absorbance at 400 nm was used as a measure of the enzyme activity. These initial rates at each time point were plotted as a function of time to obtain time-dependent exponential decay curves from which $k_{i\ obs}$ could be obtained using the equation:

$$(\text{rate})_t = (\text{rate})_{t=0} e^{(ki\ obs\ t)} + \text{offset}$$

$IC_{50}$ Enzyme Inhibition Assays

Zanamivir was obtained GlaxoSmithKline (Stevenage, UK) and oseltamivir carboxylate was obtained from oseltamivir phosphate by Dr. Keith Watson (Walter and Eliza Hall Institute, Australia). Serial ten-fold dilutions of inhibitors were prepared in water. The fluorescent substrate 4-methylumbelliferyl N-acetyl-α-D-neuraminic acid (MUNANA) was purchased from Carbosynth (UK). Enzyme inhibition assays were carried out as previously described (S. Barrett et al., *PLoS One* 6, e23627 (2011); J. L. McKimm-Breschkin et al., *Antimicrob. Chemother.* 67, 1874 (2012)) using 30 min preincubation with virus and inhibitor, then fluorescence was read after incubation with MUNANA for 60 mM The $IC_{50}$ was calculated as the inhibitor concentration resulting in a 50% reduction in fluorescent units (FU) compared to the control.

Identification of the Active Site Nucleophile of Influenza NA

Labeling and Proteolysis of NA N9

Labeling of N9 NA (1 mg/mL) was accomplished by incubating the enzyme (40 μL) in 50 mM phosphate buffer (pH 6.8), containing 2 mM 2,3-difluoro KDN (30 μL) for 30 min at room temperature. After this time, phosphate buffer (120 μL, pH 2.0) containing pepsin (0.3 mg/mL) was added. Proteolytic digestion was performed for 1 h and the sample was frozen prior to mass spectrometric analysis. A sample of unlabeled enzyme for comparison was also prepared in the same manner.

Electrospray Mass Spectrometry

Mass spectra were recorded on a PE-Sciex API 300 triple quadrupole mass spectrometer and a PE-Sciex API QSTAR pulsar (Sciex, Thornhill, Ontario, Canada) equipped with an Ionspray ion source. Peptides were separated by reverse phase HPLC on a LC Packing UltiMate Micro HPLC system (Dionex, Sunnyvale, Calif.) directly interfaced with the mass spectrometer. In each of the MS experiments, the proteolytic digest was loaded onto a C-18 column (LC Packing, 100 Å pepMap, 1 mm×150 mm) equilibrated with solvent A (solvent A: 0.05% trifluoroacetic acid—2% acetonitrile in water). Elution of the peptides was accomplished using a gradient (0%-60%) of solvent B over 60 min followed by 85% solvent B over 20 min (solvent B: 0.045% trifluoroacetic acid-80% acetonitrile in water). Solvents were pumped at a constant flow rate of 50 μL/min. Spectra were recorded in the single quadrupole scan mode (LC-MS) or the tandem MS product-ion scan mode. In the single quadrupole mode (LC-MS), the quadrupole mass analyzer was scanned over a mass-to-charge ratio (m/z) range of 100-2200 Da with a step size of 0.5 Da and a dwell time of 1.5 ms per step. The ion source voltage (ISV) was set at 5.5 kV and the orifice energy (OR) was 45 V. In the tandem MS daughter-ion scan mode, the spectra were obtained in a separate experiment by selectively introducing the labeled (m/z=1489) or unlabeled (m/z=1221) parent ion from the first quadrupole (Q1) into the collision cell (Q2) and observing the product ions in the third quadrupole (Q3). The scan range of Q3 was 100-1600, the step size was 0.5 Da, the dwell time was 1 ms, ISV was 5 kV, OR was 45 V, Q0=−10, IQ2=−48.

X-Ray Crystallography

NA from influenza virus A/NWS/Tern/Australia/G70C/75 was purified as described previously (T. J. Blick et al., *Virology* 214, 475 (1995)) and crystallized in a similar fashion to that described (W. G. layer et al., *Virology* 137, 314 (1984)) in potassium phosphate buffer (1.7 M, pH 6.7). The NA-inhibitor N9-FeqGuDFSA complex was prepared by soaking crystals in cryo-protectant solution containing well solution with 20% of glycerol and 2 mM concentration of inhibitor over 35 min at 4° C. X-ray diffraction data was collected at −173° C. at the Australian synchrotron MX1 beamline (T. M. McPhillips et al., *J. Synchrotron. Radiat.* 9, 401 (2002)) with wavelength of 0.95369 Å. The ADSC Q210 detector was set at a distance of 200 mm, 1° oscillations were taken and a total of 360 frames were obtained, with each frame given a 1 s total exposure time. The data was processed with HKL2000 (Z. Otwinowski, W. Minor, *Methods Enzymol.* 307 (1997)). A total of 2404581 (>1σ) observations were measured up to 2.0 Å and reduced to 32402 unique reflections with a merging $R_{merge}$-factor of 16.6% over all the observations with mean $\langle I\rangle/\langle\sigma(I)\rangle$ of 24.7. The space group is cubic, I432, with unit cell dimension a=180.8 (2) Å. The position of the N9 molecule was identified in the asymmetric unit by PHASER (A. J. McCoy et al., *J. Appl. Crystallogr.* 40, 658 (2007)) molecular replacement using the structure of N9 without ligand (PDB entry: 1NNC) (J. N. Varghese, V. C. Epa, P. M. Colman, *Protein Sci.* 4, 1081 (1995)). The structure with N9 molecules alone was refined and then the 3-fluoro(eq)-4-guanidino-sialyl moiety was built into the observed residual electron density. Initial refinement of the inhibitor position did not account for the all residual density observed, in particular in the region between the inhibitor and the 1406 residue. The continuous bridge of residual electron density between the C-2 atom of the inhibitor and hydroxyl oxygen OH of the aromatic side chain of Y406 residue suggested the C—O covalent bond (fig. S4) Next, the two active site species, covalently bonded and non-bonded elimination product were refined. The length of the covalent linkage for bonded species was kept at a chemically sensible value (1.4 Å) by using corresponding stereochemical restraints. The occupancies of two species were refined to 30 and 70%, respectively for bonded and non-bonded species, with sensible values of atomic B-factors. Additional water molecules in the active site and elsewhere were then identified by difference Fourier methods during the course of the refinement. Iterative refinement and model building were conducted using REFMAC (G. N. Murshudov, A. A. Vagin, E. J. Dodson, *Acta crystallogr.* 53, 240 (1997)) and MIFit (D. E. McRee, *J. Struct. Biol.* 125, 156 (1999); D. E. McRee, J. Badger, MIFit Manual 0 Rigaku, (2003-6)), and yielded a model for 388 residues for the N9 A chain with 12 attached glycans, 7 glycerol molecules from cryo-protectant, 1 calcium ion, two bound forms of the inhibitor (covalent and elimination product) and 383 water molecules. The refinement was carried out using the full data set up to 2.0 Å with a 1σ cutoff. The final $R/R_{free}$ 0.226/0.269 for the complex was 14.4/18.9% with rms deviations from ideal bonds and angles of 0.02 Å and 2.09°, respectively, and a mean B-value of 34.9 $Å^2$ for the refined non-hydrogen atoms. Progress of the refinement was monitored using the $R_{free}$ statistics based on a test set encompassing 5% of the observed diffraction amplitudes (A. T. Brünger, *Nature* 355, 472 (1992)). The coordinates of the complex have been deposited in the PDB with deposition code 3W09 and further experimental and data processing details are given in Table 3.

TABLE 3

X-ray data collection and refinement statistics.
NA9-FeqGuDFSA

| | |
|---|---|
| Beamline | AS MX1 |
| Wavelength (Å) | 0.95369 |
| Resolution range (Å) | 42.66-2.0 (2.05-2.00) |
| Space group | I432 |
| Unit cell ($a = b = c$ Å, $\alpha = \beta = \gamma = 90°$) | 180.8 (2) |
| Total reflections observed | 2404581 |
| Unique reflections | 32402 (2335) |
| Redundancy | 70 (35) |
| Completeness (%) | 99.55 (99.43) |
| $<I>/<\sigma(I)>$ | 24.7 (1.1) |
| Wilson B-factor | 53.40 |
| $R_{merge}{}^{a}$ | 0.166 (0.762) |
| $\chi^2_{merge}{}^{b}$ | 1.37 (1.18) |
| $R^c$ | 0.144 (0.267) |
| $R_{free}{}^{d}$ | 0.189 (0.294) |
| Number of atoms | 3719 |
| macromolecules | 3245 |
| ligands | 48 |
| water | 383 |
| cryo-agent | 42 |
| metal | 1 |
| Protein residues | 388 |
| RMSD (bonds) (Å) | 0.021 |
| RMSD (angles) (°) | 2.092 |
| Ramachandran favoured (%) | 95.6 |
| Ramachandran outliers (%) | 0.5 |
| Average B-factor ($Å^2$) | 34.89 |
| macromolecules | 33.26 |
| solvent | 46.51 |
| ligands | 30.85 |
| Matthews coefficient, $V_m$ ($Å^3$/Da) | 2.37 |
| Solvent (%) | 47.6 |

Statistics for the highest-resolution shell are shown in parentheses. ${}^{a}R_{merge}=\Sigma_{hkl}\Sigma_j|I_j-<1_j>|/\Sigma_{hkl}\Sigma_j|I_j|$ and ${}^{b}\chi^2_{merge}=\Sigma_{hkl}/\Sigma_j(I_j-<I_j>)^2/\Sigma_{hkl}\Sigma_j(\sigma_j{}^2+<\sigma_j>^2)$, where hkl specifies unique indices, j indicates equivalent observations of hkl, $I_j$ and $\sigma_j{}^2$ are the observed intensities and their errors, and </j> and <g> are the mean values. ${}^{c}R={}_{hkl}||F_o|-F_c|/\Sigma_{hkl}|F_o|$, where $|F_o|$ and $|F_C|$ are the observed and calculated structure factor amplitudes, respectively. [d]Represents 5% of the data.

Cell-Based Assay of Influenza Anti-Viral Activity

Madin Darby Canine Kidney (MDCK) cells were cultured as previously described (J. L. McKimm-Breschkin et al., *Antimicrob. Chemother.* 67, 1874 (2012)). Plaque assays in MDCK cells were overlaid with DMEM/F12 without serum using 0.5% immunodiffusion-grade agarose (MP Biomedicals, Australia), containing 1 mg/mL L-1-tosylamido-2-phenylethyl chloromethyl ketone ('TPCK')-treated trypsin (Worthington, USA). For plaque reduction assays (PRAs), serial ten-fold dilutions of inhibitors were incorporated into the overlay (J. L. McKimm-Breschkin et al., Antimicrob. Chemother. 67, 1874 (2012)) which consists of making serial 2-fold dilutions of the antiviral compounds (from 1:2 to 1:4096 in MegaVir medium in enough volume for the number of viruses tested–60 uL per virus), to which is added 100 infectious units of the specific influenza virus and the preparations are transferred to monolayers of MDCK cells in a microtitre plate. The assay was carried out on a 96-well microtitre plate. The plate is monitored for the development of influenza cytopathic effects from days 3 to 5 post infection, at which time the plate is fixed with 1% formalin, the agarose is removed and cells are stained with 0.05% neutral red and scanned. The $IC_{50}$ is the inhibitor concentration causing a 50% decrease in plaque size. Where there was greater than 50% reduction in plaque size between two drug concentrations a range is used. Antiviral activity is determined by the inhibition of development of cytopathic effects. The highest dilution of the compound at which the monolayers are intact is taken as the end-point. FaxGuD-FSA, Zanamivir, Oseltamivir, and Peramivir were used as controls.

Dilution Preparations:

1. In row A on a clean 96-well microtitre plate, prepare 2-fold serial dilutions of antiviral compounds from 1:2 to 1:4096 in MegaVir medium in enough volume for the number of viruses tested (60 uL per virus).
2. Transfer 55 uL of the 2-fold dilution series to a clean row in the 96-well microtitre plate.
3. To the 55 uL dilution series, add 55 uL of diluted influenza virus (at 100 $TCID_{50}$ per 25 ul). Also add virus to positive control wells.
4. To the now 110 uL mixture, add 55 uL of 4× TPCK-treated trypsin. Add trypsin also to positive and negative control wells. Mix well.
5. Prepare also 2-fold serial dilutions from 1:2 to 1:256 for the inoculating virus in
MegaVir medium for back titration.

Plate Inoculation:

6. In a 96-well microtitre plate containing confluent monolayers of MDCK cells in ~200 uL MegaVir medium, transfer 75 uL of the mixture to 2 respective rows as duplicates.
7. Transfer 50 uL of the positive control, and 25 uL of negative controls to respective wells.
8. Transfer also 25 uL of the virus back titration in duplicates.
9. Therefore in each well:
    a. Samples: 25 uL compounds+25 uL virus+25 uL trypsin
    b. Positive control: 25 uL virus+25 uL trypsin (no compounds)
    c. Negative control: 25 uL trypsin (no compounds or virus)
    d. Back titration: 25 uL virus
10. The plates are incubated at 37° C. in a $CO_2$ incubator for 3 days, then observed for the appearance of cytopathic effects on day 3 and day 5.

Viruses

The wild type and mutant viruses used in the plaque reduction assay and/or the MUNANA based enzyme inhibition assay were human strains: B/Perth/211/01 influenza B and D197E mutant (A. C. Hurt et al., *Antimicrob. Agents Chemother.* 50, 1872 (2006)), with decreased susceptibility to all NA inhibitors due to E197 affecting interactions of R152 with the N-acetyl group on the sugar ring (A. J. Oakley et al., *J. Med. Chem.* 53, 6421 (2010)); A/Mississippi/3/01 H1N1 and H275Y mutant (A. S. Monto et al., *Antimicrob. Agents Chemother.* 50, 2395 (2006)) with decreased susceptibility specifically to oseltamivir due to Y275 limiting structural changes necessary to accommodate the oseltamivir pentyl ether side chain (P. J. Collins et al., *Nature* 453, 1258 (2008)); A/Fukui/45/04 H3N2 and E119V mutant (M. Tashiro et al., *Antivir. Ther.* 14, 751 (2009)), with decreased susceptibility specifically to oseltamivir due to altered interactions of V119 with the 4-amino group on the cyclohexene ring. We also used the laboratory strain NWS/G70C H1N9, a reassortant containing the NWS HA and all other genes from A/Tern/Australia/G70C/75 and the E119G mutant, as this mutant has selective resistance to zanamivir, due to altered interactions of G119 with the 4-guanidino group (T. J. Blick et al., *Virology* 214, 475 (1995)). The NWS/G70C virus was also used as a source of purified protein for mass spectroscopy, enzyme studies and crystallized for X-ray crystallography as previously described (T. J. Blick et al., *Virology* 214, 475 (1995)). Virus was grown in eggs and the NA was proteolytically cleaved using pronase and purified by gel filtration (T. J. Blick et al., *Virology* 214, 475 (1995)).

Some of the mutants were generated by producing viruses in derivatives of zanamivir, all of which still had the 4-guanidinium group. Each of the mutants have mutations at E119. E119 interactions are significant for high affinity binding of NAIs, but each substitution often only affects binding of a subset of the inhibitors. It is already known that E119G confers zanamivir and peramivir resistance, but not oseltamivir, which is thought to be due to altered interactions with the guanidinium group, and E119V confers oseltamivir and 4-aminoNeu5Ac2en resistance, but not to zanamivir or peramivir.

Wild Type Viruses:
*A/Auckland/3/2009 (pandemic H1N1)
*B/Florida/4/2006
*A/Solomon Islands/3/2006 (seasonal H1N1)
G70C H1N9 wt
E119G Fukui H3N2 wt
sH1N1/01 H275Y
sH1N1/08 wt
B/Perth wt Mutant Viruses:
*A/Auckland/3/2009 mutant 1 E119K
*B/Florida/4/2006 mutant 1 E117D (E119D N2 numbering)
*A/Solomon Islands/3/2006 mutant E119A
NWS/G70C H1N9
Fukui H3N2 E119V
sH1N1/01 H275Y
sH1N1/08 H275Y
B/Perth D197E
*provided by Biota Holdings Limited The H275Y numbering is based on the sequence of seasonal H1N1 strains, while the H274Y numbering is based on cross referencing and alignment to the N2 strain. Generally, the H274Y numbering was how all numbering was referenced until the global spread of the H274Y H1N1 in 2007-8. However, there are several insertions and deletions between different subtypes, which made the numbering change. Accordingly, both are used and they refer to the same mutation (i.e. H275Y is the N1 numbering and the H274Y N2 numbering). The H275Y mutants referred herein were identified H274Y in the provisional from which this application claims priority.

Animal Studies

Animal studies were performed in accordance with the recommendations in the Guide to the Care and Use of Laboratory Animals of the Canadian Council on Animal Care. Ethics protocols were approved by the Animal Care Committee of the University of British Columbia (A09-0058) and the University Animal Care Committee of Simon Fraser University (956HS-10).

Pharmacokinetic Studies

Pharmacokinetics were determined in Balb/c mice (N=4 per group per time point). Compounds were administered in saline either intranasally or intravenously with a target dose of 1 mg/kg. At each time point, animals were euthanized by $CO_2$ and blood was immediately drawn by cardiac puncture, followed by organ collection. Plasma was separated from blood before storage. All tissues were analyzed by extraction of the compound (either zanamivir or FaxGuDFSA) and analysis by UPLC-MS/MS methods. The chromatography used a gradient mobile phase of A) 1% methanol in ammonium acetate and B) acetonitrile and a HILIC stationary phase column. Recovery of the analytes from tissue and limits of quantitation (based on accuracy (<25% bias) and precision (<20% RSD) were characterized for each method. FaxAmDFSA was used as an internal standard. Extractions were accomplished with a mixture of ammonium acetate and acetonitrile. For solid organs, samples were first homogenized with cycles in a BeadBeater apparatus followed by centrifugation to remove solids from the sample. Data were analyzed to determine pharmacokinetic parameters using WinNonLin 7.2.

Efficacy Study

Protective efficacy of FaxGuDFSA to influenza A virus challenge was determined in 6-week old Balb/c mice. Mouse-adapted A/Hong Kong/1/68 (H3N2) clone m20C (E. G. Brown et al., *Proc. Natl. Acad. Sci. U.S.A.* 98, 6883 (2001)) was used as the challenge virus. Mice were challenged intranasally by 1,250 pfu ($3\times LD_{50}$) virus in 10 μL DMEM. Mice were treated with either FaxGuDFSA or zanamivir intranasally twice daily (in 20 μL saline per dose) in the morning and the evening beginning 2 h prior to infection over 6 days. The intervals between treatments were approximately 8 and 16 h and thus, twelve doses in total were administered. Over the course of the experiment, mice were monitored twice daily for clinical signs and body weight. Animals were removed from the experiment when they lost 20% of body weight.

To monitor the virus replication in lung, virus RNA in the lung was quantitated by qPCR amplification of the viral M genome segment and normalization against the level of a house keeping gene, GAPDH. Lungs were harvested at predetermined time points and the RNA was extracted from the lungs (PureLink RNA Mini Kit, Ambion). The qPCR was performed with probes that are labeled with 6-FAM or TAMRA, by using QuantiFast Multiplex RT-PCR Kit (Qiagen). Primer and probe sequences are available upon request.

EXAMPLES

Further embodiments are described with reference to the following, non-limiting, examples.

Figure 2A:
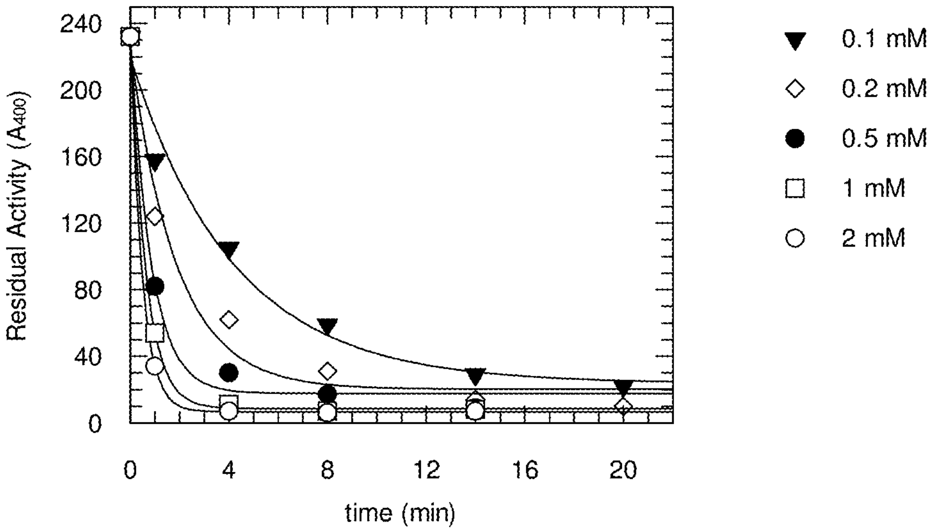
FIGS. 2A-2B include a graphical representation of (FIG. 2A) the inactivation of influenza NA N9 as a function of time upon incubation with difluoroKDN and (FIG. 2B) the spontaneous time-dependent reactivation of influenza NA N9 activity after removal of excess Difluoro KDN from difluoroKDN-inactivated NA-N9.
Figure 2B:
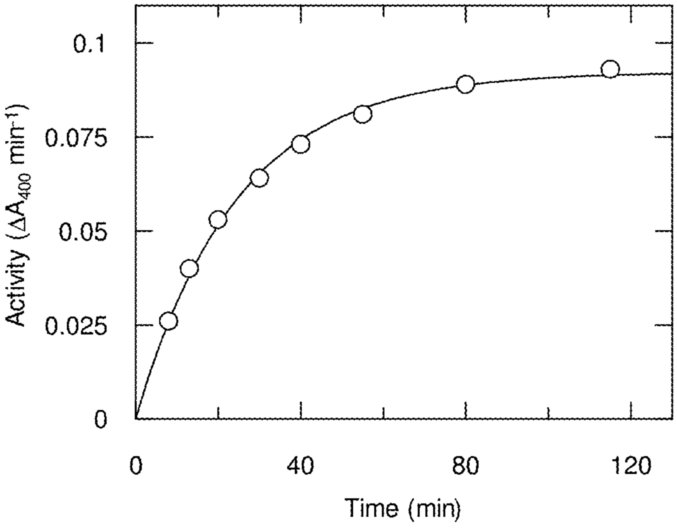
Figure 3:
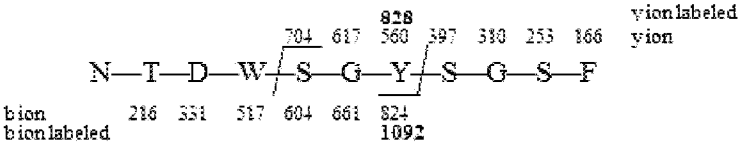
FIG. 3 is a schematic depiction of the LC/MS daughter-ion fragmentation pattern of digested influenza NA N9 inactivated with Difluoro KDN, which confirms the covalent attachment of the inhibitor to Tyr406.

Example 1: Difluorosialic Acids are Covalent NA Inhibitors that React with Y406 as the Catalytic Nucleophile NAs catalyze the hydrolysis of sialosides by a process resulting in net retention of stereochemistry at the site of substitution. As mentioned, a mechanism involving an ion-pair intermediate has long been suggested for the GH34 influenza NA (M. von Itzstein, *Nat. Rev. Drug Discov.* 6, 967 (2007)). We herein provide the first evidence for a covalent intermediate formed in the course of the reaction catalyzed by the influenza NA by use of 3-fluorosialosyl fluoride (DFSA) (FIG. 1A) as a substrate that exhibits slow turnover. The electronegative fluorine atom at C-3 inductively destabilizes the oxocarbenium ion-like transition states for both formation and hydrolysis of the intermediate, thus slowing each step, while the C-2 anomeric fluoride leaving group speeds the formation step, permitting accumulation of the covalent intermediate (FIG. 1A). Rapid inactivation of NA was observed at low inactivator concentrations, such that individual kinetic parameters ($K_i$ and $k_i$) could not be determined for the N9 NA; only a second order rate constant $k_i/K_i$ of 196 $min^{-1}$ $mM^{-1}$ could be measured (Table 4 and FIG. 2A). Turnover of the covalent intermediate ($k_{hydr}$) also occurred rapidly, with a $t_{1/2}<1$ minute (Table 4 and FIG. 2B). Confirmation of the formation of a covalent species and identification of the site of attachment was achieved by peptic digestion of N9 NA that had been labeled with 3-fluorosialyl fluoride (i.e. DFSA) or its difluoro KDN analogue (FIG. 3). Isolation and subsequent sequence analysis of the labeled peptide by LC/MS-MS identified this peptide as NTDWSGYSGSF, with the tyrosine (Y) bearing the sugar label. This provides direct evidence for a role of Y406 as the catalytic nucleophile.

TABLE 4

Inactivation and reactivation parameters for DFSA.

| Compound | Virus | $k_i/K_i$ ($min^{-1}$ $mM^{-1}$) | $t_{1/2\ (reac)}$ (min) |
|---|---|---|---|
| 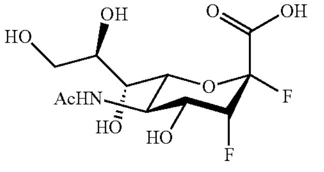 DFSA | A/NWS/G70C/75 | 196 | <1 min |

Previously published work by Hagiwara et al. (1994) reported 3-fluoro-sialic acids as being only modest sialidase inhibitors. Specifically, they report two compounds, one with an OH group at carbon 2 (position T in Formula I). However, the OH group is not a sufficiently good leaving group to allow trapping of a covalent intermediate. Accordingly, the Hagiwara et al. OH compound (at C2 equivalent to T in Formula I) showed minimal inhibition. Furthermore, the other compound tested by Hagiwara et al., which has a fluorine (a sufficient leaving group) at C2 (equivalent to T in Formula I), did not have the correct stereochemistry at C-2. Accordingly, an appreciation of these requirements was missing in Hagiwara et al.

Example 2: Selective Inhibition of Influenza Virus NA In Vitro

With the knowledge that the influenza NAs employ a covalent mechanism, we embarked on a program to explore these 2,3-difluoro sialic acids (DFSAs) as a possible new class of mechanism-based influenza therapeutics that inhibit by covalently blocking the active site. This is an attractive approach since not only can the initial affinity of the drug (KO be optimized, but also, the relative rate constants for formation ($k_i$) and hydrolysis ($k_{hydr}$) of the trapped intermediate, with the objective being to optimize the ratio of $k_i/k_{hyth}$. Such a strategy has worked well previously for the β-lactam antibiotics, and may provide particularly favorable pharmacokinetic behavior in this situation. Indeed covalent drugs are regaining respect, with three of the top-selling drugs in the U.S. being covalent inhibitors of their targets (J. Singh et al., *Nature Rev. Drug Discov.* 10, 307 (2011)). Key improvements required to convert DFSA into a useful drug candidate are therefore to introduce selectivity for the viral NA over host enzymes and to drastically reduce rates of turnover ($k_{hyth}$). Since the incorporation of an equatorial cationic nitrogen substituent at the site equivalent to OH-4 of sialic acid provided a substantial affinity boost within zanamivir and oseltamivir, it was of interest to synthesize versions of DFSA bearing amine (Am) and guanidine (Gu) substituents at C-4. Not only might these electron-withdrawing substituents improve the initial affinity and the specificity for the influenza enzyme, but also turnover of the intermediate may be further slowed, due both to the additional stabilization of the bound intermediate provided through improved interactions with the enzyme, and to the added inductive effect of the substituent on the reaction transition state. The effects of equatorial (eq) stereochemistry of F3 on inhibitory behavior were also explored.

Synthesis of the protected diastereomeric 3-equatorial-2,3-difluoro-4-azido neuraminic acids as key intermediates was achieved by Selectfluor™ hydroxyfluorination of 2,4-dideoxy-2,3-didehydro-4-azido-N-acetylneuraminic acid (4-azido-DANA) (M. von Itzstein et al., *Carbohydr. Res.* 244, 181 (1993)) followed by installation of an equatorial fluorine at C-2 using diethylaminosulfur trifluoride (DAST). The lead candidates shown in Table 2, FeqAmDFSA and FeqGuDFSA, were then prepared by reduction or reductive guanidylation, followed by deprotection.

Kinetic Parameters for NA Inhibition

Kinetic parameters for inactivation and reactivation of N1, N2 and N9 NAs, as representatives of the Group 1 and Group 2 enzymes, by several DFSA derivatives are presented in Table 5. Rate constants for turnover by hydrolysis ($k_{hyth}$) were determined by monitoring the time course of reactivation of dialyzed, inactivated enzyme, and fitting the data to a first order expression. First order rate constants for inactivation and reactivation are also expressed in the form of half-lives for each process in Table 5.

TABLE 5

Inactivation and reactivation parameters for DFSA derivatives.

| Compound | Virus[a] | $k_i/K_i$ ($min^{-1}$ $mM^{-1}$) | $K_i$ (μM) | $t_{1/2\ (inac)}$ (min) | $k_{hyd}$ ($min^{-1}$) | $t_{1/2\ (reac)}$ (min) |
|---|---|---|---|---|---|---|
| 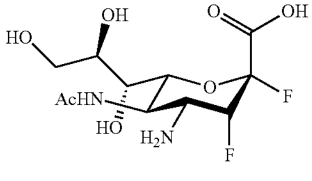 FaxAmDFSA | Brisbane H1N1 | 106 | 3.15 | 2.1 | 0.0001 | 6900 |
| | Brisbane H1N1 H275Y | 29 | 9.49 | 2.5 | 0.0002 | 3450 |
| | California H1N1 | 95 | 4.28 | 1.7 | 0.0001 | 6900 |
| | G70C H1N9 | 74 | 2.32 | 4.0 | 0.0003 | 2300 |
| | Hong Kong H3N2 | 140 | 0.24 | 20.8 | <0.0001 | >6900 |
| 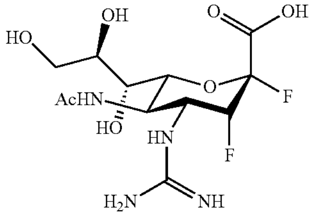 FaxGuDFSA | Brisbane H1N1 | 371 | 0.25 | 7.4 | <0.0001 | >6900 |
| | Brisbane H1N1 H275Y | 160 | 0.47 | 9.2 | <0.0001 | >6900 |
| | California H1N1 | 93 | 0.35 | 20.9 | <0.0001 | >6900 |
| | G70C H1N9 | 246 | 0.41 | 6.8 | <0.0001 | >6900 |
| | Hong Kong H3N2 | 470 | 0.07 | 20.2 | <0.0001 | >6900 |
| 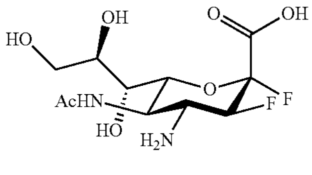 FeqAmDFSA | Brisbane H1N1 | 3479 | 0.23 | 0.9 | 0.0027 | 256 |
| | Brisbane H1N1 H275Y | 849 | 5.50 | 0.2 | 0.0059 | 117 |
| | California H1N1 | 4422 | 0.37 | 0.4 | 0.0150 | 46 |
| | G70C H1N9 | 4332 | 0.21 | 0.8 | 0.0140 | 49 |
| | Hong Kong H3N2 | 5662 | — | — | 0.0045 | 153 |
| 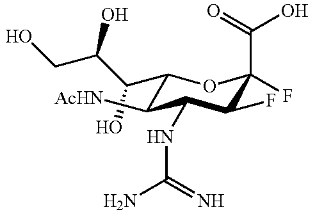 FeqGuDFSA | Brisbane H1N1 | 5812 | 0.35 | 0.3 | 0.0005 | 1380 |
| | Brisbane H1N1 | 2992 | 0.5 | 0.5 | 0.0015 | 460 |
| | H275Y | | 0.1 | 0.9 | 0.001 | 690 |
| | California H1N1 | 7594 | | | | |
| | G70C H1N9 | 3879 | 0.35 | 0.5 | 0.0019 | 363 |
| | Hong Kong H3N2 | 5737 | 0.15 | 0.8 | 0.0005 | 1380 |

[a]Brisbane H1N1 = A/Brisbane/59/07;
Brisbane H1N1 H275Y = A/Brisbane/59/07 oseltamivir-resistant;
California H1N1 = A/California/07/09;
G70C H1N9 = A/NWS/G70C/75;
Hong Kong H3N2 = A/HongKong/01/68;
[b]N.D. = Not Determined.

Incorporation of the charged substituent at C-4 result in high initial affinity and greatly reduces the rate constant for reactivation of enzymes inactivated by the compounds in Table 5. Half-lives for reactivation of NAs labeled by these compounds ranged from 0.75 h to >100 h. These very slow turnover rates are extremely important as they mean that the virus will remain inactivated for extended times, even after the compound may have been cleared from relevant tissues, with favorable consequences for pharmacokinetic behavior.

Figure 1B:
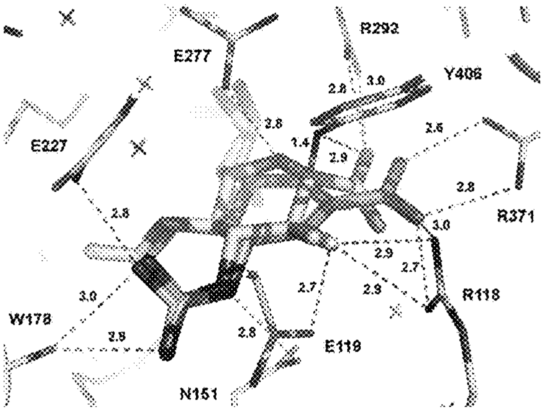
Figure 1C:
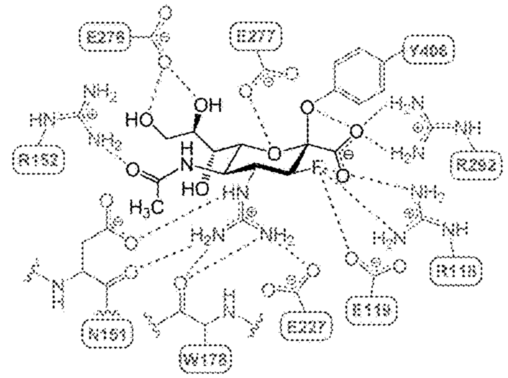

Interestingly, compounds with an equatorial fluorine at C-3 inactivate significantly faster than do those with an axial fluorine. Further, the presence of a guanidine substituent at C-4 slows both the inactivation and reactivation more than does an amine substituent, with a much greater effect on the reactivation step. The half lives of 2-4 hours are expected to be sufficient for 3F equatorial compounds to function well in vivo. Since the two transition states (for formation and hydrolysis) will be very similar, this difference in rate likely has its origins in optimized interactions of the guanidine with the active site at the stage of the covalent intermediate, as is seen in the crystal structure of the trapped species shown in FIG. 1B. A covalent bond of 1.45 Å is clearly observed in the electron density map (not shown), between C-2 of 3-fluoro (eq) sialic acid and the phenolic oxygen of Y406. As observed previously in a structure of the GH33 sialidase NanI (S. L. Newstead et al., *J. Biol. Chem.* 283, 9080 (2008)), the covalent intermediate species is accompanied by an unsaturated form of fluorosialic acid formed by elimination. The carboxylate groups of both bound species form electrostatic interactions with the guanidine groups of the strictly conserved arginine triad R118, R292 and R371, a key interaction common among existing NA inhibitors. However, the elimination product forms stronger interactions (≤3 Å) with R118 and R371 similar to those formed with zanamivir, while the covalent intermediate exhibits shorter contacts (≤3 Å) with R292 (FIG. 1B). In addition to many other interactions that have been observed in previous complexes of N9 NA with zanamivir (J. N. Varghese et al., *Protein Sci.* 4, 1081 (1995)), both forms of FeqGuDFSA also form electrostatic interactions at 2.9 Å (FIG. 1B) between the equatorial fluorine and the positive charge of the guanidine group of R118, reminiscent of those seen in other protein/ligand systems (J. A. K. Howard et al., *Tetrahedron* 52, 12613 (1996)), possibly explaining the higher initial affinity of the FeqGuDFSA inhibitor compared to others. The C-4 guanidine indeed forms strong interactions with the anionic pocket, very similar to those found with zanamivir (M. von Itzstein et al., *Nature* 363, 418 (1993)), thereby contributing to stabilization of the intermediate.

Comparison of NA Inhibition $IC_{50}$ values were measured for each of DFSA and its derivatives, as well as zanamivir and oseltamivir carboxylate (oseltamivir from which the pro-drug ester had been hydrolyzed), against the NA of different virus strains after pre-incubation for 30 minutes prior to substrate addition. The $IC_{50}$ values so obtained are presented in Tables 6-10, along with data for mutant viruses to be discussed below.

TABLE 6

Effects of mutations at E119A, D, K on sensitivity to inhibitors ($IC_{50}$ μM)

| | B/Florida | | | Sol Isl sH1N1 | | | Auckland pH1N1 | | |
|---|---|---|---|---|---|---|---|---|---|
| nM | wt | E119D | Fold Res | wt | E119A | Fold Res | wt | E119K | Fold Res |
| Zanamivir | 3.9 | >10,000 | ≥10,000 | 2.2 | >10,000 | ≥10,000 | 0.6 | >100,000 | ≥100,000 |
| Oseltamivir | 22.6 | 1205 | 53 | 1.0 | 419 | 419 | 0.2 | 147 | 613 |
| FaxGuDFSA | 6.6 | 1515 | 229 | 181 | >10,000 | >1000 | 284 | >100,000 | >1000 |
| FeqGuDFSA | 2.0 | 27 | 13 | 4.7 | 130 | 27 | 4.0 | >100,000 | ≥10,000 |

The results shown in TABLE 6 are consistent with previous testing of other panels of viruses with FaxGuDFSA. Notably, the FeqGuDFSA has a lower $IC_{50}$ than the FaxGuDFSA for many of the resistant strains.

The E119K mutation appears to confer some resistance to both FaxGuDFSA and FeqGuDFSA, but less so to oseltamivir (4-$NH_2$), suggesting that the interactions of the 4-guanidinium group are potentially significant to high affinity binding of not only the established NAIs but also to both FaxGuDFSA and FeqGuDFSA. Thus the 3F in the equatorial position results in significantly different binding behaviour for the FeqGuDFSA compared to the other inhibitors with a 4-G group.

For the E119D there is lower resistance with the FeqGuDFSA than the FaxGuDFSA, and importantly also several orders of magnitude lower resistance than to zanamivir. Since the E119D is significantly less resistant to FeqGuDFSA than to zanamivir, this suggests the guanidinium in the fluorosialics is less likely to select for resistant strains than that in zanamivir, likely due to the different (transient covalent) mode of action.

TABLE 7

Effects of mutations at E119G, V on sensitivity to inhibitors ($IC_{50}$ μM)

| | G70C H1N9 wt | G70C H1N9 E119G | Fold resistance | Fukui H3N2 wt | Fukui H3N2 E119V | Fold resistance |
|---|---|---|---|---|---|---|
| Zanamivir | 2.7 | 678 | 248 | 3.8 | 3.4 | 0.9 |
| Oseltamivir | 2.8 | 2.9 | 1.1 | 1.7 | 260 | 155 |

TABLE 7-continued

Effects of mutations at E119G, V on sensitivity to inhibitors ($IC_{50}$ μM)

| | G70C H1N9 wt | G70C H1N9 E119G | Fold resistance | Fukui H3N2 wt | Fukui H3N2 E119V | Fold resistance |
|---|---|---|---|---|---|---|
| FaxGuDFSA | 66.7 | 1433 | 21 | 2006 | 998 | 0.5 |
| FeqGuDFSA | 136 | 17.3 | 0.1 | 24.9 | 2.4 | 0.1 |

The E119G mutation appears to confer a high level resistance to zanamivir only, confers 20-fold resistance to FaxGuDFSA, whereas the FeqGuDFSA actually appears to bind better in the mutant than in the wild type.

The E119V mutation appears to confer a high level resistance to Oseltamivir, but does not confer resistance to the FaxGuDFSA, zanamivir, or FeqGuDFSA.

TABLE 8

Effects of H275Y mutation on sensitivity to inhibitors ($IC_{50}$ nM)

| | sH1N1/01 wt | sH1N/01 H275Y | Fold resistance | sH1N1/08 wt | sH1N1/08 H275Y | Fold resistance |
|---|---|---|---|---|---|---|
| Zanamivir | 1.9 | 2.2 | 1.2 | 1.0 | 2.0 | 2.0 |
| Oseltamivir | 3.1 | 2440 | 781 | 3.0 | 2000 | 667 |
| FaxGuDFSA | 115.4 | 217 | 1.9 | 136 | 265 | 1.9 |
| FeqGuDFSA | 12.6 | 43.5 | 3.5 | 6.8 | 43.2 | 6.4 |

FaxGuDFSA or FeqGuDFSA appear to still be effective against the H275Y mutation which confers high level oseltamivir resistance, but not to zanamivir.

TABLE 9

Effects of D197E mutation on sensitivity to inhibitors (nM)

| | B/Perth wt | B/Perth D197E | Fold resistance |
|---|---|---|---|
| Zanamivir | 8.9 | 257.5 | 28.9 |
| Oseltamivir | 104.4 | 708.0 | 6.8 |
| FaxGuDFSA | 54.0 | 161.9 | 3.0 |
| FeqGuDFSA | 4.5 | 8.0 | 1.8 |

Mutations at D197E appears to confer cross resistance to known NAIs due to altered interactions with the adjacent R152 and the N-acetyl group on the ring. However, the FeqGuDFSA does not appear to be affected by this interaction.

As shown in Table 10, comparison between pairs of DFSA derivatives again confirms that, in almost all cases, each compound with an equatorial fluorine is a superior inhibitor to its epimer with an axial fluorine, indicating that, under these conditions, improved rates of inactivation are important. Likewise, in each case the guanidine derivative showed superior performance to its amine analogue. Consequently, FeqGuDFSA was the optimal derivative within the series. Comparison of these $IC_{50}$ values with those for zanamivir and oseltamivir reveals that, on this measure, the compounds with an equatorial fluorine are of comparable efficacy, particularly when the guanidine is present. Further, their "on-rates" are superior to those of zanamivir, while off-rates are enormously slower (M. von Itzstein et al., *Nature* 363, 418 (1993); P. J. Collins et al., *Nature* 453, 1258 (2008); E. van der Vries et al., *PLoS Pathog.* 9, (2012)).

TABLE 10

$IC_{50}$ values (nM) in the enzyme inhibition assay for wild type and mutant pairs.

| Virus[a] | Zanamivir | Oseltamivir | DFSA | FaxAmDFSA | FaxGuDFSA | FeqAmDFSA | FeqGuDFSA |
|---|---|---|---|---|---|---|---|
| B/Perth | 8.9 | 104.4 | 70 | 210 | 54 | 5.4 | 4.5 |
| B/Perth D197E | 257.5 | 708.0 | 170 | 340 | 162 | 16 | 8 |
| A/Mississippi H1N1 | 1.9 | 3.1 | 80 | 840 | 115 | 45 | 13 |
| A/Mississippi H1N1 H275Y | 2.2 | 2440 | 120 | 2210 | 217 | 86 | 44 |
| A/Fukui H3N2 | 3.8 | 1.7 | 1380 | 4710 | 2006 | 71 | 25 |
| A/Fukui H3N2 E119V | 3.4 | 260.0 | 240 | 2440 | 998 | 265 | 2.4 |
| G70C H1N9 | 2.7 | 2.8 | 1190 | 2700 | 66.7 | 270 | 140 |
| G70C H1N9 E119G | 678.4 | 2.9 | 1150 | 1600 | 1433 | 73 | 17 |

The $IC_{50}$ is the concentration of inhibitor which reduces enzyme activity by 50% compared to the control uninhibited value. Values are the means of duplicate assays.

[a]B/Perth = B/Perth/211/01; B/Perth D197E = B/Perth/211/01 oseltamivir-resistant; A/Mississippi H1N1 = A/Mississippi/3/01; A/Mississippi H1N1 H275Y = A/Mississippi/3/01 oseltamivir-resistant; A/Fukui H3N2 = A/Fukui/45/01; A/Fukui H3N2 E119V = A/Fukui/45/01oseltamivir-resistant; G70C H1N9 = A/NWS/G70C/75; G70C H1N9 E119G = A/NWS/G70C/75 zanamivir-resistant.

Inhibitor Specificity

The specificity of these inhibitors was then evaluated by testing them against Neu2 as a representative human NA (all human NAs belong to the sequence-related family GH33). No inactivation of Neu2 was seen with either of the amine derivatives, and inactivation by FaxGuDFSA and FeqGuDFSA occurred slowly, but at rates some $10^5$-$10^6$ lower than inactivation of NA at comparable concentrations. This behavior is a considerable improvement over zanamivir, which inhibits Neu2 with a $K_i$ of 17 μM (22).

As seen above, the 3' equatorial compounds are better at maintaining potency against some viral strains than the 3' axial counterparts. Furthermore, various resistant strains of virus appear to remain sensitive to the 3' equatorial compounds even when sensitivity diminishes for the 3' axial compounds. In addition, the amine is generally expected to have better oral bioavailability than the guanidine.

Example 3: Effects on Influenza Virus Replication and Efficacy Against Resistant Strains Based upon these very promising results the ability of our DFSA derivatives to inhibit the replication of the virus in cell culture was explored using MDCK cells. Three A strains (N1, N2 and N9) plus one B strain were tested in plaque size reduction assays (PRA), with zanamivir used as a control. While absolute sensitivity in the PRA depends on both the affinity of the HA for cell receptors as well as the NA function (J. L. McKimm-Breschkin, *Antiviral Res.* 47, 1 (2000); M. Tisdale, *Rev. Med. Virol.* 10, 45 (2000)), it is a useful assay for determining relative sensitivity to inhibitors. The PRA showed that all DFSA derivatives inhibited virus replication (Table 11) with no cytotoxicity observed even at 5 mM concentrations of the derivatives. The H3N2 virus was less susceptible to all inhibitors compared to the other strains, due to the lower affinity of its HA, which allows viral spread with less NA activity (C. I. Thompson et al., *J. Antimicrob. Chemother.* 53, 759 (2004)). However, for all strains, substitution with the 4-amino enhanced inhibition over the parent DFSA, and the 4-guanidino substitution further enhanced inhibition of virus replication. It is interesting that the stereochemistry of the fluorine substituent had little effect on efficacy for the compounds with a 4-amine substituent, apart from possibly a small enhancement with the B virus. However the presence of an equatorial fluorine in the 4-guanidine version resulted in a further 10-fold enhancement in potency for three strains tested, the one exception being G70C (H1N9), which was particularly well inhibited by the axial version also. Consequently, FeqGuDFSA had the highest potency of all of the inhibitors, including zanamivir, against the influenza B virus and performed comparably against the influenza A strains. Two points are particularly noteworthy at this stage. One is that this behavior in PRA largely mirrors the in vitro kinetic data, with the compounds possessing an equatorial fluorine being superior to those with an axial fluorine, and the 4-guanidine substitution being superior to a 4-amino. The other is that the absolute $IC_{50}$ values in these PRAs are consistently lower than those for enzyme inhibition for all except FeqAmDFSA and impressively in all cases are in the low nanomolar range. The relatively poor PRA data observed with FeqAmDFSA likely reflects the faster reactivation of NA inactivated by this compound.

TABLE 11

IC$_{50}$ values in the plaque size reduction assay.

| Virus[a] | Zanamivir | DFSA | FaxAmDFSA | FaxGuDFSA | FeqAmDFSA | FeqGuDFSA |
|---|---|---|---|---|---|---|
| B/Perth | 10 nM | 1 μM | 100 nM | 10-100 nM | 10-100 nM | 1 nM |
| A/Mississippi H1N1 | ≤1 nM | 1 μM | 100 nM | 10 nM | 100 nM | 1 nM |
| A/Fukui H3N2 | 100 nM | 100 μM | 1 μM | 100 nM | 1 μM | 10 nM |
| G70C H1N9 | 1-10 nM | 1-10 μM | 1 μM | 1-10 nM | 1 μM | 10 nM |

The IC$_{50}$ is the concentration of inhibitor required to reduce plaque size by 50%. Values are the means of duplicate assays.
[a]B/Perth = B/Perth/211/01; A/Mississippi H1N1 = A/Mississippi/3/01; A/Fukui H3N2 = A/Fukui/45/01; G70C H1N9 = A/NWS/G70C/75.

The DFSA derivatives proved effective in vitro against a series of resistant strains, with the FeqGuDFSA again proving to be the most widely active (Tables 6-10). All compounds proved effective against virus with the H275Y mutation that affects binding of the isopentyl side chain of oseltamivir, as might be predicted. This is also reflected in the very similar kinetic data measured for each DFSA derivative with another H275Y oseltamivir resistant strain and its parent (Tables 4 and 5). While the E119G mutation, which affects interactions with the inhibitor's guanidine (J. N. Varghese et al., Structure 6, 735 (1998)) led to a 20-fold reduction in efficacy of FaxGuDFSA, this was much less severe than the 250-fold reduction in zanamivir binding. The effectiveness of the FeqGuDFSA is particularly noteworthy, and highlights the different resistance profiles and modes of action of the DFSAs and zanamivir. Clearly, selection against transition state analogue binding (zanamivir) does not suppress covalent intermediate formation. Indeed in the case of the E119 mutations that target the 4-position, FeqGuDFSA actually performed 10-fold better against the mutant strains than against the wild type. This most likely reflects slower reactivation of the trapped intermediate formed on the mutant, due to disruption of transition state-stabilizing interactions. This excellent profile against otherwise resistant strains is extremely promising and supports the concept of mechanism-based inhibition as a means to minimize selection of resistant strains.

Example 4: In Vivo Efficacy Studies

Prior to in vivo efficacy studies in mouse models, the pharmacokinetic properties of FaxGuDFSA as a representative DFSA derivative were evaluated for administration by intravenous and intranasal routes, and compared with data collected in parallel for zanamivir. Levels of FaxGuDFSA in blood, lung and trachea were measured and half lives determined. Intranasal dosing resulted in 92% bioavailability compared to that seen with intravenous injection, along with approximately seven times higher peak concentrations (Cmax) and ten times higher total exposure (AUC$_{(0-120\ mm)}$) in both lung and trachea compared to the intravenous route. Further, the plasma half-life of FaxGuDFSA was also significantly longer after intranasal administration than after IV injection (Table 12). The general similarity of this pharmacokinetic behavior to that of zanamivir, consistent with the similar polarities of the two compounds, encouraged us to test the efficacy via intranasal administration, using zanamivir as our control.

TABLE 12

Pharmacokinetic data on distribution of analytes after intranasal delivery.

| Analyte | Assay parameter | Plasma | Lung | Trachea |
|---|---|---|---|---|
| Zanamivir | Recovery | 31% | 55% | Not evaluated |
|  | LOQ[a] | 5 ng/mL | 20 ng/g | 500 ng/g |
|  | Gradient (A > B) | 85 > 45% | 80 > 40% |  |
| FaxGuDFSA | Recovery | 102% | 74% | 69% |
|  | LOQ[a] | 5 ng/mL | 4 ng/g | 50 ng/g |
|  | Gradient (A >B) |  | 98 > 30% |  |

[a]LOQ = Limit of quantitation.

Figure 4A:
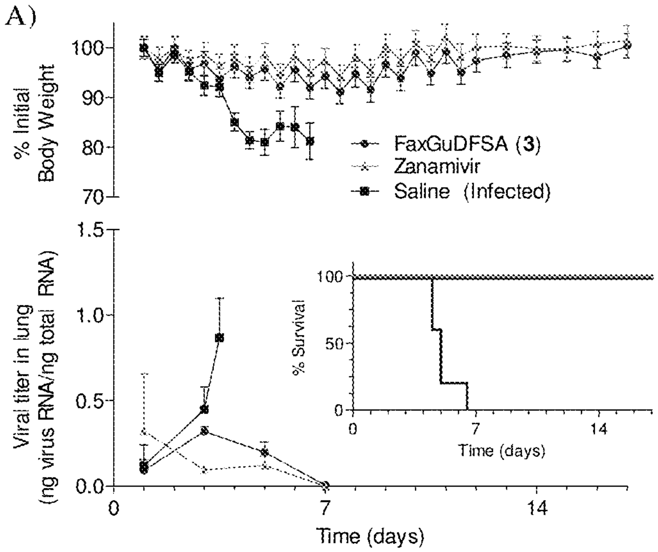
FIGS. 4A-4B include a graphical representation of the efficacy of FaxGuDFSA, FeqGuDFSA and zanamivir in treating H3N2 influenza infection in the Balb/c mouse. The top graph of FIG. 4A shows body weight over the 17 day observation period. Animals that lost 20% of initial weight were recorded as non-survivors, as indicated in the survival plot (inset). In a parallel set of animals (bottom graph of FIG. 4A), viral RNA loads were measured over 7 days by qPCR. In this group, all untreated animals survived only 3 days.

Efficacy tests were conducted using a mouse-adapted influenza A virus strain, A/Hong Kong/1/68 (H3N2) (E. G. Brown et al., Proc. Natl. Acad. Sci. U.S.A. 98, 6883 (2001)). Balb/c mice were treated with either DFSA derivative, zanamivir or saline twice daily by intranasal administration, starting two hours prior to infection. Body weights and general condition were monitored and when the animals lost 20% body weight they were euthanized and scored as non-survivors. In an initial study using 1 mg/kg/day of DFSA derivatives FaxGuDFSA showed superior results to FaxAmDFSA in prolonging the survival of animals. When FaxGuDFSA was tested at a higher dose of 10 mg/kg/day it protected all the mice from the lethal infection, as did zanamivir (FIG. 4A). In order to confirm that the compounds were acting as anti-viral agents, the viral RNA loads in lung tissue were measured by qPCR. These results confirmed that survival was indeed associated with suppression of viral replication, in a similar manner to the effect of zanamivir.

Figure 4B:
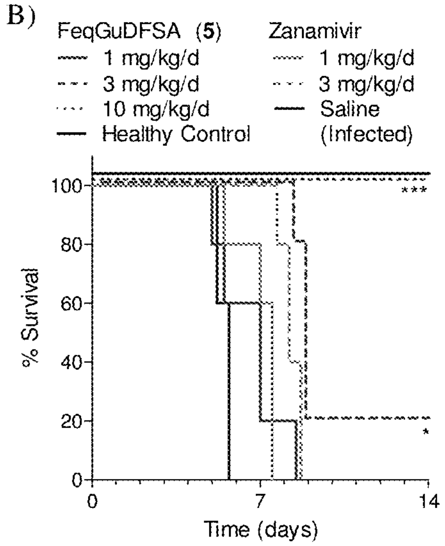

Dose-dependency of FeqGuDFSA in the protection of mice was demonstrated with 100% efficacy at 10 mg/kg/day and less protection at lower doses (FIG. 4B and Table 13). The compounds induced no ill-effect in the treated animals during the experiments compared to the saline control.

TABLE 13

Efficacy of DFSAs with H3N2 influenza-infected mice.

| Treatment | Dose (mg/kg/d) | Delay in time to endpoint relative to untreated infected control[‡] | Survival Frequency (N, %) |
|---|---|---|---|
| Evaluation of FaxGuDFSA at 10 mg/kg/d dose, N = 10 per group ||||
| Untreated Infected control | 0 | 1 | 0 |
| Zanamivir | 10 | N/A | 100[†] |
| FaxGuDFSA | 10 | N/A | 100[†] |
| Evaluation of FeqGuDFSA at 1, 3 & 10 mg/kg/d dose, N = 5 per group ||||
| Untreated Infected Control | 0 | 1 | 0 |

TABLE 13-continued

Efficacy of DFSAs with H3N2 influenza-infected mice.

| Treatment | Dose (mg/kg/d) | Delay in time to endpoint relative to untreated infected control‡ | Survival Frequency (N, %) |
|---|---|---|---|
| Untreated Uninfected Control | 0 | N/A | 100† |
| Zanamivir | 1 | 1.2* | 0 |
| | 3 | 1.7*** | 0 |
| FeqGuDFSA | 1 | 1.2 | 0 |
| | 3 | 1.5*** | 20†† |
| | 10 | N/A | 100† |

‡Delay in time to endpoint is expressed in terms of fold change relative to the untreated infected control group in each experiment (1, 2 or 3). When all animals survived and did not reach the endpoint, no delay was calculated, denoted with "N/A". In experiment #1 the humane endpoint was established at 15% body weight loss whereas in experiments #2 and 3, the endpoint was 20% body weight loss.

*Statistically significant delay in mean time to reach the endpoint (1-way ANOVA $p < 0.05$).

***Statistically significant delay in mean time to reach the endpoint (1-way ANOVA $p < 0.001$).

†All groups treated with a 10 mg/kg/d dose of NAI were 100% protected from reaching the humane endpoint, which was statistically significant (Mantel-Cox $p < 0.0001$).

††FeqGuDFSA at 3 mg/kg/d gave 20% protection from reaching the endpoint, which was statistically significant (Mantel-Cox $p < 0.004$).

CONCLUSIONS

The enzyme $IC_{50}$ kinetics, reactivation, plaque reduction assays and cross-resistance data all suggest the FeqGuDFSA is a superior inhibitor to the FaxGuDFSA. Resistance data also supports the FeqGuDFSA as having a different resistance profile than zanamivir, oseltamivir, and FaxGuDFSA. Thus the 3' equatorial F leads to novel interactions of the 4-G group at the ground and transition states, thus avoiding resistance seen with many mutations at E119. Fluorinated compounds of the class described herein are inhibitors of a range of glycosidases, and specific with respect to their target enzymes. These compounds are mechanism-based in their inhibitory action. They bind to the enzyme like the normal substrate and undergo the first step of catalysis (intermediate formation) like the natural substrate, but then only very slowly undergo the second step (turnover via hydrolysis). Importantly, this mechanism-basis inhibition should make resistance formation by viruses more difficult. Since the inhibitors are mechanism-based, any mutations in the viral enzyme that reduce the inhibition must necessarily reduce the efficiency of the enzyme on the natural substrate. Please note that the sialic acid numbering is different from that of aldose-sugars due to the anomeric carboxylate.

The fluorosialics described herein differ fundamentally from zanamivir and oseltamivir in two major ways. Zanamivir and oseltamivir are reversibly binding inhibitors that interact with the enzyme active site very tightly due to their flattened, cyclic conformation. Their binding mode likely imitates the transition state conformation of the sugar during hydrolysis. They are therefore transition state mimics. The fluorosialics described herein, by contrast, contain no double bond thus adopt a regular chair conformation. They react with the enzyme as if they are substrates and form a covalent bond with the active site nucleophile, and only hydrolyse to products very slowly. They derive their very high efficacies primarily from the long-lived nature of the intermediate formed.

It was not evident that a 3' equatorial F substituent would increase the effectiveness of these compounds against resistant viral strains strains as compared to stereoisomers having 3' axial F configuration.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention.

REFERENCES

Amaya, M. F., Watts, A., Damager, I., Wehenkel, A., Nguyen, T., Buschiazzo, A., Paris, G., Frasch, A. C., Withers, S. G. and Alzari, P. M. "Structural insights into the catalytic mechanism of *Trypanosoma cruzi* trans-sialidase" (2004) Structure, 12, 775-784.

Bantia S, Parker C D, Ananth S L, Horn L L, Andries K, Chand P, Kotian P L, Dehghani A, El-Kattan Y, Lin T, Hutchison T L, Montgomery J A, Kellog D L, Babu Y S. "Comparison of the anti-influenza virus activity of RWJ-270201 with those of oseltamivir and zanamivir." Antimicrob Agents Chemother. (2001) 45(4):1162-7.

Barrett, S. et al., *PLoS One* 6, e23627 (2011). Blick, T. J. et al., *Virology* 214, 475 (1995).

Brown, E. G. et al., *Proc. Natl. Acad. Sci. U.S.A.* 98, 6883 (2001)

Brünger, A. T. *Nature* 355, 472 (1992).

Buchini, S., Buschiazzo, A., Withers, S. G. "Towards a New Generation of Specific *Trypanosoma cruzi* Trans-sialidase Inhibitors" (2008) Angew. Chemie 47, 2700-2703.

Cantarel B L, Coutinho P M, Rancurel C, Bernard T, Lombard V, Henrissat B (2009) "The Carbohydrate-Active EnZymes database (CAZy): an expert resource for Glycogenomics". *Nucleic Acids Res* 37:D233-238.

Chandler, M. et al., *J. Chem. Soc.-Perkin Trans.* 1, 1173 (1995).

Chavas, L. M. et al., *J. Med. Chem.* 53, 2998 (2010).

Collins, P. J. et al., *Nature* 453, 1258 (2008).

Damager, I., Buchini, S., Amaya, M. L., Buschiazzo, A., Alzari, P., Frasch, A. C. Watts, A.

Withers, S. G. "Kinetic and Mechanistic Analysis of *Trypanosoma cruzi* Trans-sialidase Reveals a Classical Ping-Pong Mechanism with Acid/Base Catalysis" (2008) Biochemistry, 47, 3507-3512.

Eshaghi, A. et al., *Emerg. Infect. Dis.* 17, 1472 (2011).

Gubareva, L. V. et al., *J. Virol.* 71, 3385 (1997).

Hagiwara et al. "Inhibition of bacterial and viral sialidases by 3-fluoro-N-acetylneuraminic acid" *Carbohydrate Research* (1994) 263:167-172; and Buchini et al. Agnew. Chem. Int. Ed. (2008) 47:2700-2703.

Henrissat B, Davies G J (1997) "Structural and sequence-based classification of glycoside hydrolases". *Curr. Op. Struct. Biol.* 7:637-644.

Howard, J. A. K. et al., *Tetrahedron* 52, 12613 (1996).

Hurt, A. C. et al., *Antimicrob. Agents Chemother.* 50, 1872 (2006).

Ikeda, K.; Kitani., S.; Sato, K. Suzuki, T.; Hosokawa, C. Suzuki, Y. Tanaka, K.; Sato, M. "2b,3b-difluoro acid derivatives structurally modified at the C-4 position: synthesis and biological evaluation as inhibitors of human parainfluenza virus type 1" *Carbohydrate Res.* 2004, 339, 1367.

Kiso, M. et al., *Lancet* 364, 759 (2004).

von Itzstein. M. et al., *Nature* 363, 418 (1993).

von Itzstein, M. et al., *Carbohydr. Res.* 244, 181 (1993).

von Itzstein, M. "The war against influenza: discovery and development of sialidase inhibitors" Nature Reviews Drug Discovery (2007) 6(12): 967-974.

Laver, W. G. et al., *Virology* 137, 314 (1984).

Leatherbarrow, R., *Erithacus Software Ltd., 4th Edition, Staines*, U K, (1990).

Leneva I A, Goloubeva O, Fenton R J, Tisdale M, Webster R G. "Efficacy of zanamivir against avian influenza A viruses that possess genes encoding H5N1 internal proteins and are pathogenic in mammals." Antimicrob Agents Chemother. (2001) 45(4):1216-24.

McCoy, A. J. et al., *J. Appl. Crystallogr.* 40, 658 (2007).

McRee, D. E., *J. Struct. Biol.* 125, 156 (1999).

McRee, D. E., Badger, J., MIFit Manual© *Rigaku*, (2003-6).

McKimm-Breschkin, J. L. et al., *J. Virol.* 72, 2456 (1998).

McKimm-Breschkin, J. L., *Antiviral Res.* 47, 1 (2000).

McKimm-Breschkin, J. L. et al, *J. Antimicrob. Chemother.* 67, 1874 (2012).

McPhillips, T. M. et al., *J. Synchrotron. Radian* 9, 401 (2002).

Monto, A. S. et al., *Antimicrob. Agents Chemother.* 50, 2395 (2006).

Murshudov, G. N. et al., *Acta crystallogr.* 53, 240 (1997).

Newstead, S., Potter, J. A., Wilson, J. C., Xu, G., Chien, C.-H., Watts, A., Withers, S. G. and Taylor, G. L. "The structure of *Clostridium perfringens* NanI sialidase and its catalytic intermediates" (2008) *J. Biol. Chem.* 283, 9080-9088.

Nguyen, H. T. et al., *Clin. Infect. Dis.* 51, 983 (2010).

Oakley, A. J. et al., *J. Med. Chem.* 53, 6421 (2010).

Otwinowski, Z., Minor, W., *Methods Enzymol.,* 307 (1997).

Santana, A. G. et al., *J. Org. Chem.* 75, 5371 (2010). Singh, J. et al., *Nature Rev. Drug*

Discov. 10, 307 (2011).

Tashiro, M. et al., *Antivir. Ther.* 14, 751 (2009).

Thompson, C. I. et al., *J. Antimicrob. Chemother.* 53, 759 (2004)

Tisdale M. "Monitoring of viral susceptibility: new challenges with the development of influenza N A inhibitors." (2000) *Rev Med Virol.* 10(1):45-55.

Varghese, J. N. et al., *Protein Sci.* 4, 1081 (1995).

Varghese, J. N. et al., *Structure* 6, 735 (1998). van der Vries, E. et al., *N. Engl. J. Med.* 363, 1381 (2010). van der Vries, E. et al., *PLoS Pathog.* 9, (2012).

Watts, A. G., Oppezzo, P., Withers, S. G., Alzari, P. M. and Buschiazzo, A. "Structural and Kinetic Analysis of two Covalent Sialosyl-Enzyme Intermediates on *Trypanosoma rangeli* Sialidase" (2006) J. Biol. Chem., 281, 4149-4155.

Watts, A. G., Damager, I., Amaya, M. L., Buschiazzo, A., Alzari, P., Frasch, A. C and Withers, S. G. "*Trypanosoma cruzi* Trans-sialidase Operates through a Covalent Sialyl-Enzyme Intermediate: Tyrosine is the Catalytic Nucleophile" (2003) *J. Am. Chem. Soc.,* 125, 7532-7533.

Watts, A. G. and Withers, S. G. "The Synthesis of some Mechanistic Probes for Sialic Acid Processing Enzymes and the Labeling of a Sialidase from *Trypanosoma* rangeli" (2004) Can. J. Chem. 82, 1581-1588.

Withers, S. G. and Aebersold, R. "Approaches to labeling and identification of active site residues in glycosidases" (1995) Protein Science (Invited review) 4, 361-372.

What is claimed is:

1. A method of treating a viral infection comprising administering to a subject in need thereof an effective amount of a compound of formula I:

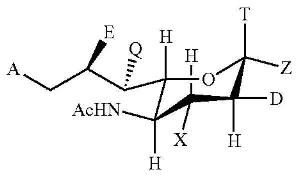

I or an effective amount of a pharmaceutically acceptable salt thereof wherein

T is COOH or COOEt;

Z is F;

D is F;

X is $NHC(NH)NH_2$;

Q is OH;

E is OH; and

A is OH, and wherein the viral infection is caused, at least in part, by an influenza virus that is resistant to zanamivir, oseltamivir, or peramivir, or a combination thereof.

2. The method of claim 1, wherein the influenza virus is resistant to zanamivir.

3. The method of claim 1, wherein the influenza virus is resistant to oseltamivir.

4. The method of claim 1, wherein the influenza virus is resistant to peramivir.

5. The method of claim 1, wherein T is COOH, and wherein the influenza virus is an H1N1, H3N2 or H1N9 subtype.

6. The method of claim 1, wherein T is COOH, and wherein the influenza virus is resistant to zanamivir.

7. The method of claim 1, wherein T is COOH, and wherein the influenza virus is resistant to oseltamivir.

8. The method of claim 1, wherein T is COOH, and wherein the influenza virus is resistant to peramivir.

9. The method of claim 1, wherein T is COOH, and wherein the influenza virus is an influenza B virus.

10. The method of claim 1, wherein T is COOEt.

11. The method of claim 10, wherein the influenza virus is an H1N1, H3N2 or H1N9 subtype.

12. The method of claim 10, wherein the influenza virus is resistant to zanamivir.

13. The method of claim 10, wherein the influenza virus is resistant to oseltamivir.

14. The method of claim 10, wherein the influenza virus is resistant to peramivir.

15. The method of claim 10, wherein the influenza virus is an influenza B virus.

16. A method of treating a viral infection comprising administering to a subject in need thereof an effective amount of a compound of formula I:

I
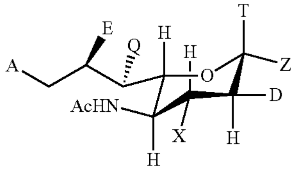
or an effective amount of a pharmaceutically acceptable salt thereof,
wherein
T is COOH or COOEt;
Z is F;
D is F;
X is $NHC(NH)NH_2$;
Q is OH;
E is OH; and
A is OH,
and wherein the viral infection is caused, at least in part, by an influenza B virus.
17. The method of claim 16, wherein T is COOEt.
* * * * *